United States Patent
Kaifosh et al.

(10) Patent No.: US 11,337,652 B2
(45) Date of Patent: May 24, 2022

(54) SYSTEM AND METHOD FOR MEASURING THE MOVEMENTS OF ARTICULATED RIGID BODIES

(71) Applicant: Facebook Technologies, LLC, Menlo Park, CA (US)

(72) Inventors: Patrick Kaifosh, New York, NY (US); Timothy Machado, Palo Alto, CA (US); Thomas Reardon, New York, NY (US); Erik Schomburg, Brooklyn, NY (US); Calvin Tong, Seattle, WA (US)

(73) Assignee: Facebook Technologies, LLC, Menlo Park, CA (US)

( * ) Notice: Subject to any disclaimer, the term of this patent is extended or adjusted under 35 U.S.C. 154(b) by 793 days.

(21) Appl. No.: 15/659,504

(22) Filed: Jul. 25, 2017

(65) Prior Publication Data

US 2018/0020978 A1   Jan. 25, 2018

Related U.S. Application Data

(60) Provisional application No. 62/366,426, filed on Jul. 25, 2016.

(51) Int. Cl.
*A61B 5/00* (2006.01)
*G01C 21/18* (2006.01)
(Continued)

(52) U.S. Cl.
CPC .......... *A61B 5/6813* (2013.01); *A61B 5/1114* (2013.01); *A61B 5/7275* (2013.01);
(Continued)

(58) Field of Classification Search
CPC ..... A61B 5/6813; A61B 5/1114; A61B 5/744; A61B 5/1112; A61B 2562/0219;
(Continued)

(56) References Cited

U.S. PATENT DOCUMENTS

| 4,055,168 A | 10/1977 | Miller et al. |
| 4,896,120 A | 1/1990 | Kamil |

(Continued)

FOREIGN PATENT DOCUMENTS

| CA | 2902045 A1 | 8/2014 |
| CA | 2921954 A1 | 2/2015 |

(Continued)

OTHER PUBLICATIONS

International Search Report and Written Opinion for International Application No. PCT/US2017/043686 dated Oct. 6, 2017.
(Continued)

*Primary Examiner* — Regis J Betsch
*Assistant Examiner* — Jeremy A Delozier
(74) *Attorney, Agent, or Firm* — FisherBroyles, LLP

(57) ABSTRACT

A method for determining spatial information for a multi-segment articulated rigid body system having at least an anchored segment and a non-anchored segment coupled to the anchored segment, each segment in the multi-segment articulated rigid body system representing a respective body part of a user, the method comprising: obtaining signals recorded by a first autonomous movement sensor coupled to a body part of the user represented by the non-anchored segment; providing the obtained signals as input to a trained statistical model and obtaining corresponding output of the trained statistical model; and determining, based on the corresponding output of the trained statistical model, spatial information for at least the non-anchored segment of the multi-segment articulated rigid body system. Determining the spatial information may include determining the position and/or orientation of the non-anchored segment relative to the anchor point and/or determining a spatial relationship between the anchored and non-anchored segments.

19 Claims, 9 Drawing Sheets

(51) Int. Cl.
*G06F 3/01* (2006.01)
*A61B 5/11* (2006.01)
*G06K 9/00* (2022.01)
*G06K 9/62* (2022.01)
*G16H 50/50* (2018.01)
*G01C 17/38* (2006.01)

(52) U.S. Cl.
CPC .............. *A61B 5/744* (2013.01); *G01C 21/18* (2013.01); *G06F 3/011* (2013.01); *G06F 3/014* (2013.01); *G06F 3/017* (2013.01); *G06K 9/00335* (2013.01); *G06K 9/6287* (2013.01); *G16H 50/50* (2018.01); *A61B 5/1112* (2013.01); *A61B 5/6824* (2013.01); *A61B 2562/0219* (2013.01); *G01C 17/38* (2013.01)

(58) Field of Classification Search
CPC .. A61B 5/6824; G06K 9/00335; G01C 21/18; G06F 3/014
See application file for complete search history.

(56) References Cited

U.S. PATENT DOCUMENTS

| | | | |
|---|---|---|---|
| 5,625,577 | A | 4/1997 | Kunii et al. |
| 6,005,548 | A | 12/1999 | Latypov et al. |
| 6,009,210 | A | 12/1999 | Kand |
| 6,244,873 | B1 | 6/2001 | Hill et al. |
| 6,411,843 | B1 | 6/2002 | Zarychta |
| 6,658,287 | B1 | 12/2003 | Litt et al. |
| 6,720,984 | B1 | 4/2004 | Jorgensen et al. |
| 6,774,885 | B1 | 8/2004 | Even-Zohar |
| 6,942,621 | B2 | 9/2005 | Avinash et al. |
| 7,089,148 | B1 | 8/2006 | Bachmann et al. |
| 7,351,975 | B2 | 4/2008 | Brady et al. |
| 7,574,253 | B2 | 8/2009 | Edney et al. |
| 7,580,742 | B2 | 8/2009 | Tan et al. |
| 7,787,946 | B2 | 8/2010 | Stahmann et al. |
| 7,805,386 | B2 | 9/2010 | Greer |
| 7,901,368 | B2 | 3/2011 | Flaherty et al. |
| 8,170,656 | B2 | 5/2012 | Tan et al. |
| 8,190,249 | B1 | 5/2012 | Gharieb et al. |
| 8,311,623 | B2 | 11/2012 | Sanger |
| 8,351,651 | B2 | 1/2013 | Lee |
| 8,421,634 | B2 | 4/2013 | Tan et al. |
| 8,435,191 | B2 | 5/2013 | Barboutis et al. |
| 8,437,844 | B2 | 5/2013 | Syed Momen et al. |
| 8,447,704 | B2 | 5/2013 | Tan et al. |
| 8,484,022 | B1 | 7/2013 | Vanhoucke |
| 8,718,980 | B2 | 5/2014 | Garudadri et al. |
| 8,744,543 | B2 | 6/2014 | Li et al. |
| 8,754,862 | B2 | 6/2014 | Zaliva |
| D717,685 | S | 11/2014 | Bailey et al. |
| 8,880,163 | B2 | 11/2014 | Barachant et al. |
| 8,890,875 | B2 | 11/2014 | Jammes et al. |
| 8,892,479 | B2 | 11/2014 | Tan et al. |
| 9,037,530 | B2 | 5/2015 | Tan et al. |
| D742,272 | S | 11/2015 | Bailey et al. |
| 9,218,574 | B2 | 12/2015 | Phillipps et al. |
| 9,235,934 | B2 | 1/2016 | Mandella et al. |
| 9,240,069 | B1 | 1/2016 | Li |
| 9,278,453 | B2 | 3/2016 | Assad |
| 9,299,248 | B2 | 3/2016 | Lake et al. |
| D756,359 | S | 5/2016 | Bailey et al. |
| 9,351,653 | B1 | 5/2016 | Harrison |
| 9,367,139 | B2 | 6/2016 | Ataee et al. |
| 9,372,535 | B2 | 6/2016 | Bailey et al. |
| 9,389,694 | B2 | 7/2016 | Ataee et al. |
| 9,408,316 | B2 | 8/2016 | Bailey et al. |
| 9,459,697 | B2 | 10/2016 | Bedikian et al. |
| 9,483,123 | B2 | 11/2016 | Aleem et al. |
| 9,597,015 | B2 | 3/2017 | McNames et al. |
| 9,600,030 | B2 | 3/2017 | Bailey et al. |
| 9,612,661 | B2 | 4/2017 | Wagner et al. |
| 9,613,262 | B2 | 4/2017 | Holz |
| 9,654,477 | B1 | 5/2017 | Kotamraju |
| 9,659,403 | B1 | 5/2017 | Horowitz |
| 9,687,168 | B2 | 6/2017 | John |
| 9,696,795 | B2 | 7/2017 | Marcolina et al. |
| 9,720,515 | B2 | 8/2017 | Wagner et al. |
| 9,741,169 | B1 | 8/2017 | Holz |
| 9,766,709 | B2 | 9/2017 | Holz |
| 9,785,247 | B1 | 10/2017 | Horowitz et al. |
| 9,788,789 | B2 | 10/2017 | Bailey |
| 9,864,431 | B2 | 1/2018 | Keskin et al. |
| 9,867,548 | B2 | 1/2018 | Le et al. |
| 9,880,632 | B2 | 1/2018 | Ataee et al. |
| 9,891,718 | B2 | 2/2018 | Connor |
| 10,042,422 | B2 | 8/2018 | Morun et al. |
| 10,070,799 | B2 | 9/2018 | Ang et al. |
| 10,078,435 | B2 | 9/2018 | Noel |
| 10,101,809 | B2 | 10/2018 | Morun et al. |
| 10,152,082 | B2 | 12/2018 | Bailey |
| 10,188,309 | B2 | 1/2019 | Morun et al. |
| 10,199,008 | B2 | 2/2019 | Aleem et al. |
| 10,203,751 | B2 | 2/2019 | Keskin et al. |
| 10,216,274 | B2 | 2/2019 | Chapeskie et al. |
| 10,251,577 | B2 | 4/2019 | Morun et al. |
| 10,310,601 | B2 | 6/2019 | Morun et al. |
| 10,331,210 | B2 | 6/2019 | Morun et al. |
| 10,362,958 | B2 | 7/2019 | Morun et al. |
| 10,409,371 | B2 | 9/2019 | Kaifosh et al. |
| 10,437,335 | B2 | 10/2019 | Daniels |
| 10,460,455 | B2 | 10/2019 | Giurgica-Tiron et al. |
| 10,489,986 | B2 | 11/2019 | Kaifosh et al. |
| 10,496,168 | B2 | 12/2019 | Kaifosh et al. |
| 10,504,286 | B2 | 12/2019 | Kaifosh et al. |
| 2003/0144829 | A1 | 7/2003 | Geatz et al. |
| 2003/0171921 | A1 | 9/2003 | Manabe et al. |
| 2003/0184544 | A1 | 10/2003 | Prudent |
| 2004/0054273 | A1 | 3/2004 | Finneran et al. |
| 2004/0092839 | A1 | 5/2004 | Shin et al. |
| 2006/0129057 | A1 | 6/2006 | Maekawa et al. |
| 2007/0009151 | A1 | 1/2007 | Pittman et al. |
| 2007/0172797 | A1 | 7/2007 | Hada et al. |
| 2007/0177770 | A1 | 8/2007 | Derchak et al. |
| 2007/0256494 | A1 | 11/2007 | Nakamura et al. |
| 2007/0285399 | A1 | 12/2007 | Lund |
| 2008/0051673 | A1 | 2/2008 | Kong et al. |
| 2008/0052643 | A1 | 2/2008 | Ike et al. |
| 2008/0103639 | A1 | 5/2008 | Troy et al. |
| 2008/0214360 | A1 | 9/2008 | Stirling et al. |
| 2008/0221487 | A1 | 9/2008 | Zohar et al. |
| 2008/0285805 | A1* | 11/2008 | Luinge ................. A61B 5/1122 382/107 |
| 2009/0027337 | A1 | 1/2009 | Hildreth |
| 2009/0079813 | A1 | 3/2009 | Hildreth |
| 2009/0082692 | A1 | 3/2009 | Hale et al. |
| 2009/0082701 | A1 | 3/2009 | Zohar et al. |
| 2009/0112080 | A1 | 4/2009 | Matthews |
| 2009/0124881 | A1 | 5/2009 | Rytky |
| 2009/0326406 | A1 | 12/2009 | Tan et al. |
| 2009/0327171 | A1 | 12/2009 | Tan et al. |
| 2010/0030532 | A1 | 2/2010 | Arora et al. |
| 2010/0063794 | A1 | 3/2010 | Hernandez-Rebollar |
| 2010/0106044 | A1* | 4/2010 | Linderman .......... A61B 5/0488 600/546 |
| 2010/0113910 | A1 | 5/2010 | Brauers et al. |
| 2010/0280628 | A1 | 11/2010 | Sankai |
| 2010/0292595 | A1 | 11/2010 | Paul |
| 2010/0292606 | A1 | 11/2010 | Prakash et al. |
| 2010/0292617 | A1 | 11/2010 | Lei et al. |
| 2010/0293115 | A1 | 11/2010 | Seyed Momen |
| 2010/0315266 | A1 | 12/2010 | Gunawardana et al. |
| 2011/0077484 | A1 | 3/2011 | Van Slyke et al. |
| 2011/0092826 | A1 | 4/2011 | Lee et al. |
| 2011/0173204 | A1 | 7/2011 | Murillo et al. |
| 2011/0173574 | A1 | 7/2011 | Clavin et al. |
| 2011/0230782 | A1 | 9/2011 | Bartol et al. |
| 2012/0066163 | A1 | 3/2012 | Balls et al. |
| 2012/0188158 | A1 | 7/2012 | Tan et al. |
| 2012/0265480 | A1 | 10/2012 | Oshima |
| 2012/0283526 | A1 | 11/2012 | Gommesen et al. |
| 2013/0004033 | A1 | 1/2013 | Trugenberger |

(56) References Cited

U.S. PATENT DOCUMENTS

| | | |
|---|---|---|
| 2013/0077820 A1 | 3/2013 | Marais et al. |
| 2013/0123656 A1 | 5/2013 | Heck |
| 2013/0141375 A1 | 6/2013 | Ludwig et al. |
| 2013/0207889 A1 | 8/2013 | Chang et al. |
| 2013/0217998 A1 | 8/2013 | Mahfouz et al. |
| 2013/0232095 A1* | 9/2013 | Tan ............ G06F 3/015 706/12 |
| 2013/0317382 A1 | 11/2013 | Le |
| 2013/0317648 A1 | 11/2013 | Assad |
| 2014/0052150 A1 | 2/2014 | Taylor et al. |
| 2014/0092009 A1 | 4/2014 | Yen et al. |
| 2014/0098018 A1* | 4/2014 | Kim ............ G06F 3/014 345/156 |
| 2014/0196131 A1 | 7/2014 | Lee |
| 2014/0198034 A1 | 7/2014 | Bailey et al. |
| 2014/0198035 A1 | 7/2014 | Bailey et al. |
| 2014/0223462 A1 | 8/2014 | Aimone et al. |
| 2014/0240103 A1 | 8/2014 | Lake et al. |
| 2014/0240223 A1 | 8/2014 | Lake et al. |
| 2014/0245200 A1 | 8/2014 | Holz |
| 2014/0249397 A1 | 9/2014 | Lake et al. |
| 2014/0277622 A1 | 9/2014 | Raniere |
| 2014/0278441 A1 | 9/2014 | Ton et al. |
| 2014/0297528 A1 | 10/2014 | Agrawal et al. |
| 2014/0304665 A1 | 10/2014 | Holz |
| 2014/0330404 A1 | 11/2014 | Abdelghani et al. |
| 2014/0334083 A1 | 11/2014 | Bailey |
| 2014/0344731 A1 | 11/2014 | Holz |
| 2014/0355825 A1 | 12/2014 | Kim et al. |
| 2014/0358024 A1 | 12/2014 | Nelson et al. |
| 2014/0361988 A1 | 12/2014 | Katz et al. |
| 2014/0364703 A1 | 12/2014 | Kim et al. |
| 2014/0365163 A1 | 12/2014 | Jallon |
| 2014/0376773 A1 | 12/2014 | Holz |
| 2015/0006120 A1 | 1/2015 | Sett et al. |
| 2015/0010203 A1 | 1/2015 | Muninder et al. |
| 2015/0025355 A1 | 1/2015 | Bailey et al. |
| 2015/0029092 A1 | 1/2015 | Holz et al. |
| 2015/0035827 A1 | 2/2015 | Yamaoka et al. |
| 2015/0045689 A1 | 2/2015 | Barone |
| 2015/0045699 A1 | 2/2015 | Mokaya et al. |
| 2015/0051470 A1 | 2/2015 | Bailey et al. |
| 2015/0057770 A1 | 2/2015 | Bailey et al. |
| 2015/0070270 A1 | 3/2015 | Bailey et al. |
| 2015/0070274 A1 | 3/2015 | Morozov |
| 2015/0084860 A1 | 3/2015 | Aleem et al. |
| 2015/0109202 A1 | 4/2015 | Ataee et al. |
| 2015/0124566 A1 | 5/2015 | Lake et al. |
| 2015/0128094 A1 | 5/2015 | Baldwin et al. |
| 2015/0141784 A1 | 5/2015 | Morun et al. |
| 2015/0148641 A1 | 5/2015 | Morun et al. |
| 2015/0157944 A1 | 6/2015 | Gottlieb |
| 2015/0169074 A1 | 6/2015 | Ataee et al. |
| 2015/0182165 A1 | 7/2015 | Miller et al. |
| 2015/0193949 A1 | 7/2015 | Katz et al. |
| 2015/0223716 A1 | 8/2015 | Korkala et al. |
| 2015/0234426 A1 | 8/2015 | Bailey et al. |
| 2015/0261306 A1 | 9/2015 | Lake |
| 2015/0261318 A1 | 9/2015 | Scavezze et al. |
| 2015/0277575 A1 | 10/2015 | Ataee et al. |
| 2015/0296553 A1 | 10/2015 | DiFranco et al. |
| 2015/0302168 A1 | 10/2015 | De Sapio et al. |
| 2015/0309563 A1 | 10/2015 | Connor |
| 2015/0309582 A1 | 10/2015 | Gupta |
| 2015/0313496 A1 | 11/2015 | Connor |
| 2015/0325202 A1 | 11/2015 | Lake et al. |
| 2015/0332013 A1 | 11/2015 | Lee et al. |
| 2015/0346701 A1 | 12/2015 | Gordon et al. |
| 2015/0366504 A1 | 12/2015 | Connor |
| 2015/0370326 A1 | 12/2015 | Chapeskie et al. |
| 2015/0370333 A1 | 12/2015 | Ataee et al. |
| 2016/0011668 A1 | 1/2016 | Gilad-Bachrach et al. |
| 2016/0049073 A1 | 2/2016 | Lee |
| 2016/0092504 A1 | 3/2016 | Mitri et al. |
| 2016/0144172 A1 | 5/2016 | Hsueh et al. |
| 2016/0162604 A1 | 6/2016 | Xioli et al. |
| 2016/0187992 A1 | 6/2016 | Yamamoto et al. |
| 2016/0235323 A1 | 8/2016 | Tadi et al. |
| 2016/0239080 A1* | 8/2016 | Marcolina ............ G06F 3/011 |
| 2016/0262687 A1 | 9/2016 | Imperial |
| 2016/0274758 A1 | 9/2016 | Bailey |
| 2016/0275726 A1 | 9/2016 | Mullins |
| 2016/0292497 A1 | 10/2016 | Kehtarnavaz et al. |
| 2016/0313798 A1* | 10/2016 | Connor ............ G06F 3/017 |
| 2016/0313801 A1* | 10/2016 | Wagner ............ G06F 3/017 |
| 2016/0313890 A1 | 10/2016 | Walline et al. |
| 2016/0313899 A1 | 10/2016 | Noel |
| 2016/0350973 A1 | 12/2016 | Shapira et al. |
| 2017/0031502 A1 | 2/2017 | Rosenberg et al. |
| 2017/0035313 A1 | 2/2017 | Hong et al. |
| 2017/0061817 A1 | 3/2017 | Mettler May |
| 2017/0068445 A1 | 3/2017 | Lee et al. |
| 2017/0080346 A1 | 3/2017 | Abbas |
| 2017/0090604 A1 | 3/2017 | Barbier |
| 2017/0091567 A1 | 3/2017 | Wang et al. |
| 2017/0119472 A1 | 5/2017 | Herrmann et al. |
| 2017/0123487 A1 | 5/2017 | Hazra et al. |
| 2017/0124816 A1 | 5/2017 | Yang et al. |
| 2017/0161635 A1* | 6/2017 | Oono ............ G06N 7/005 |
| 2017/0188980 A1 | 7/2017 | Ash |
| 2017/0259167 A1 | 9/2017 | Cook et al. |
| 2017/0285756 A1 | 10/2017 | Wang et al. |
| 2017/0285848 A1 | 10/2017 | Rosenberg et al. |
| 2017/0296363 A1 | 10/2017 | Yetkin et al. |
| 2017/0301630 A1 | 10/2017 | Nguyen et al. |
| 2017/0308118 A1 | 10/2017 | Ito |
| 2017/0344706 A1 | 11/2017 | Torres et al. |
| 2017/0347908 A1 | 12/2017 | Watanabe et al. |
| 2018/0000367 A1 | 1/2018 | Longinotti-Buitoni |
| 2018/0020951 A1 | 1/2018 | Kaifosh et al. |
| 2018/0024634 A1 | 1/2018 | Kaifosh et al. |
| 2018/0024635 A1 | 1/2018 | Kaifosh et al. |
| 2018/0064363 A1 | 3/2018 | Morun et al. |
| 2018/0067553 A1 | 3/2018 | Morun et al. |
| 2018/0081439 A1 | 3/2018 | Daniels |
| 2018/0088765 A1 | 3/2018 | Bailey |
| 2018/0092599 A1 | 4/2018 | Kerth et al. |
| 2018/0095630 A1 | 4/2018 | Bailey |
| 2018/0101235 A1 | 4/2018 | Bodensteiner et al. |
| 2018/0101289 A1 | 4/2018 | Bailey |
| 2018/0120948 A1 | 5/2018 | Aleem et al. |
| 2018/0140441 A1 | 5/2018 | Poirters |
| 2018/0150033 A1 | 5/2018 | Lake et al. |
| 2018/0153430 A1 | 6/2018 | Ang et al. |
| 2018/0153444 A1 | 6/2018 | Yang et al. |
| 2018/0154140 A1 | 6/2018 | Bouton et al. |
| 2018/0178008 A1 | 6/2018 | Bouton et al. |
| 2018/0301057 A1 | 10/2018 | Hargrove et al. |
| 2018/0307314 A1 | 10/2018 | Connor |
| 2018/0321745 A1 | 11/2018 | Morun et al. |
| 2018/0321746 A1 | 11/2018 | Morun et al. |
| 2018/0333575 A1 | 11/2018 | Bouton |
| 2018/0344195 A1 | 12/2018 | Morun et al. |
| 2018/0360379 A1 | 12/2018 | Harrison et al. |
| 2019/0008453 A1 | 1/2019 | Spoof |
| 2019/0025919 A1 | 1/2019 | Tadi et al. |
| 2019/0033967 A1 | 1/2019 | Morun et al. |
| 2019/0033974 A1 | 1/2019 | Mu et al. |
| 2019/0038166 A1 | 2/2019 | Tavabi et al. |
| 2019/0076716 A1 | 3/2019 | Chiou et al. |
| 2019/0121305 A1 | 4/2019 | Kaifosh et al. |
| 2019/0121306 A1 | 4/2019 | Kaifosh et al. |
| 2019/0146809 A1 | 5/2019 | Lee et al. |
| 2019/0150777 A1 | 5/2019 | Guo et al. |
| 2019/0192037 A1 | 6/2019 | Morun et al. |
| 2019/0212817 A1 | 7/2019 | Kaifosh et al. |
| 2019/0223748 A1 | 7/2019 | Al-natsheh et al. |
| 2019/0227627 A1 | 7/2019 | Kaifosh et al. |
| 2019/0228330 A1 | 7/2019 | Kaifosh et al. |
| 2019/0228533 A1 | 7/2019 | Giurgica-Tiron et al. |
| 2019/0228579 A1 | 7/2019 | Kaifosh et al. |
| 2019/0228590 A1 | 7/2019 | Kaifosh et al. |
| 2019/0228591 A1 | 7/2019 | Giurgica-Tiron et al. |
| 2019/0247650 A1 | 8/2019 | Tran |

(56) References Cited

U.S. PATENT DOCUMENTS

| | | | |
|---|---|---|---|
| 2019/0324549 | A1 | 10/2019 | Araki et al. |
| 2019/0357787 | A1 | 11/2019 | Barachant et al. |
| 2019/0362557 | A1 | 11/2019 | Lacey et al. |

FOREIGN PATENT DOCUMENTS

| | | | |
|---|---|---|---|
| CA | 2939644 A1 | 8/2015 | |
| CN | 1838933 A | 9/2006 | |
| CN | 103777752 A | 5/2014 | |
| CN | 105190578 A | 12/2015 | |
| CN | 106102504 A | 11/2016 | |
| EP | 2198521 B1 | 6/2012 | |
| EP | 2959394 A1 | 12/2015 | |
| EP | 3104737 A1 | 12/2016 | |
| JP | H05-277080 A | 10/1993 | |
| JP | 2005-095561 A | 4/2005 | |
| JP | 2010-520561 A | 6/2010 | |
| JP | 2016-507851 A | 3/2016 | |
| JP | 2017-509386 A | 4/2017 | |
| KR | 2015-0123254 A | 11/2015 | |
| KR | 2016-0121552 A | 10/2016 | |
| KR | 10-1790147 B1 | 10/2017 | |
| WO | WO 2008/109248 A2 | 9/2008 | |
| WO | WO 2009/042313 A1 | 4/2009 | |
| WO | WO 2010/104879 A2 | 9/2010 | |
| WO | WO 2012/155157 A1 | 11/2012 | |
| WO | WO 2014/130871 A1 | 8/2014 | |
| WO | WO 2014/186370 A1 | 11/2014 | |
| WO | WO 2014/194257 A1 | 12/2014 | |
| WO | WO 2014/197443 A1 | 12/2014 | |
| WO | WO 2015/027089 A1 | 2/2015 | |
| WO | WO 2015/073713 A1 | 5/2015 | |
| WO | WO 2015/081113 A1 | 6/2015 | |
| WO | WO 2015/123445 A1 | 8/2015 | |
| WO | WO 2015/199747 A1 | 12/2015 | |
| WO | WO 2016/041088 A1 | 3/2016 | |
| WO | WO 2017/062544 A1 | 4/2017 | |
| WO | WO 2017/092225 A1 | 6/2017 | |
| WO | WO 2017/120669 A1 | 7/2017 | |
| WO | Wo 2017/172185 A1 | 10/2017 | |
| WO | WO 2017/208167 A1 | 12/2017 | |

OTHER PUBLICATIONS

International Preliminary Report on Patentability for International Application No. PCT/US2017/043686 dated Feb. 7, 2019.
International Search Report and Written Opinion for International Application No. PCT/US2017/043693 dated Oct. 6, 2017.
International Preliminary Report on Patentability for International Application No. PCT/US2017/043693 dated Feb. 7, 2019.
International Search Report and Written Opinion for International Application No. PCT/US2017/043791 dated Oct. 5, 2017.
International Preliminary Report on Patentability for International Application No. PCT/US2017/043791 dated Feb. 7, 2019.
International Search Report and Written Opinion for International Application No. PCT/US2017/043792 dated Oct. 5, 2017.
International Preliminary Report on Patentability for International Application No. PCT/US2017/043792 dated Feb. 7, 2019.
International Search Report and Written Opinion for International Application No. PCT/US2018/056768 dated Jan. 15, 2019.
International Search Report and Written Opinion for International Application No. PCT/US2018/061409 dated Mar. 12, 2019.
Benko et al., Enhancing Input On and Above the Interactive Surface with Muscle Sensing. The ACM International Conference on Interactive Tabletops and Surfaces. ITS '09. 2009:93-100.
Boyali et al., Spectral Collaborative Representation based Classification for hand gestures recognition on electromyography signals. Biomedical Signal Processing and Control. 2016;24:11-18.
Cheng et al., A Novel Phonology- and Radical-Coded Chinese Sign Language Recognition Framework Using Accelerometer and Surface Electromyography Sensors. Sensors. 2015;15:23303-24.
Csapo et al., Evaluation of Human-Myo Gesture Control Capabilities in Continuous Search and Select Operations. 7th IEEE International Conference on Cognitive Infocommunications. 2016;000415-20.
Delis et al., Development of a Myoelectric Controller Based on Knee Angle Estimation. Biodevices 2009. International Conference on Biomedical Electronics and Devices. Jan. 17, 2009. 7 pages.
Diener et al., Direct conversion from facial myoelectric signals to speech using Deep Neural Networks. 2015 International Joint Conference on Neural Networks (IJCNN). Oct. 1, 2015. 7 pages.
Ding et al., HMM with improved feature extraction-based feature parameters for identity recognition of gesture command operators by using a sensed Kinect-data stream. Neurocomputing. 2017;262:108-19.
Farina et al., Man/machine interface based on the discharge timings of spinal motor neurons after targeted muscle reinnervation. Nature. Biomedical Engineering. 2017;1:1-12.
Gallina et al., Surface EMG Biofeedback. Surface Electromyography: Physiology, Engineering, and Applications. 2016:485-500.
Jiang, Purdue University Graduate School Thesis/Dissertation Acceptance. Graduate School Form 30. Updated Jan. 15, 2015. 24 pages.
Kawaguchi et al., Estimation of Finger Joint Angles Based on Electromechanical Sensing of Wrist Shape. IEEE Transactions on Neural Systems and Rehabilitation Engineering. 2017;25(9):1409-18.
Kim et al., Real-Time Human Pose Estimation and Gesture Recognition from Depth Images Using Superpixels and SVM Classifier. Sensors. 2015;15:12410-27.
Koerner, Design and Characterization of the Exo-Skin Haptic Device: A Novel Tendon Actuated Textile Hand Exoskeleton. 2017. 5 pages.
Li et al., Motor Function Evaluation of Hemiplegic Upper-Extremities Using Data Fusion from Wearable Inertial and Surface EMG Sensors. Sensors. MDPI. 2017;17(582):1-17.
Mcintee, A Task Model of Free-Space Movement-Based Geastures. Dissertation. Graduate Faculty of North Carolina State University. Computer Science. 2016. 129 pages.
Naik et al., Source Separation and Identification issues in bio signals: A solution using Blind source seperation. Intech. 2009. 23 pages.
Naik et al., Subtle Hand gesture identification for HCI using Temporal Decorrelation Source Separation BSS of surface EMG. Digital Image Computing Techniques and Applications. IEEE Computer Society. 2007;30-7.
Negro et al., Multi-channel intramuscular and surface EMG decomposition by convolutive blind source separation. Journal of Neural Engineering. 2016;13:1-17.
Saponas et al., Demonstrating the Feasibility of Using Forearm Electromyography for Muscle-Computer Interfaces. CHI 2008 Proceedings. Physiological Sensing for Input. 2008:515-24.
Saponas et al., Enabling Always-Available Input with Muscle-Computer Interfaces. UIST '09. 2009:167-76.
Saponas et al., Making Muscle-Computer Interfaces More Practical. CHI 2010: Brauns and Brawn. 2010:851-4.
Sauras-Perez et al., A Voice and Pointing Gesture Interaction System for Supporting Human Spontaneous Decisions in Autonomous Cars. Clemson University. All Dissertations. 2017. 174 pages.
Shen et al., I am a Smartwatch and I can Track my User's Arm. University of Illinois at Urbana-Champaign. MobiSys' 16. 12 pages.
Son et al., Evaluating the utility of two gestural discomfort evaluation methods. PLOS One. 2017. 21 pages.
Strbac et al., Microsoft Kinect-Based Artificial Perception System for Control of Functional Electrical Stimulation Assisted Grasping. Hindawi Publishing Corporation. BioMed Research International. 2014. 13 pages.
Torres, Myo Gesture Control Armband. PCMag. Https://www.pcmag.com/article2/0,2817,2485462,00.asp 2015. 9 pages.
Wodzinski et al., Sequential Classification of Palm Gestures Based on A* Algorithm and MLP Neural Network for Quadrocopter Control. Metrol. Meas. Syst., 2017;24(2):265-76.

(56) References Cited

OTHER PUBLICATIONS

Xue et al., Multiple Sensors Based Hand Motion Recognition Using Adaptive Directed Acyclic Graph. Applied Sciences. MDPI. 2017;7(358):1-14.
PCT/US2017/043686, Oct. 6, 2017, Internatioanl Search Report and Written Opinion.
PCT/US2017/043686, Feb. 7, 2019, International Preliminary Report on Patentability.
PCT/US2017/043693, Oct. 6, 2017, International Search Report and Written Opinion.
PCT/US2017/043693, Feb. 7, 2019, International Preliminary Report on Patentability.
PCT/US2017/043791, Oct. 5, 2017, International Search Report and Written Opinion.
PCT/US2017/043791, Feb. 7, 2019, International Preliminary Report on Patentability.
PCT/US2017/043792, Oct. 5, 2017, International Search Report and Written Opinion.
PCT/US2017/043792, Feb. 7, 2019, International Preliminary Report on Patentability.
PCT/US2018/056768, Jan. 15, 2019, International Search Report and Written Opinion.
PCT/US2018/061409, Mar. 12, 2019, International Search Report and Written Opinion.
PCT/US2018/063215, Mar. 21, 2019, International Search Report and Written Opinion.
PCT/US2019/015134, May 15, 2019, International Search Report and Written Opinion.
PCT/US2019/015167, May 21, 2019, International Search Report and Written Opinion.
PCT/US2019/015174, May 21, 2019, International Search Report and Written Opinion.
PCT/US2019/015238, May 16, 2019, International Search Report and Written Opinion.
PCT/US2019/015183, May 3, 2019, International Search Report and Written Opinion.
PCT/US2019/015180, May 28, 2019, International Search Report and Written Opinion.
PCT/US2019/015244, May 16, 2019, International Search Report and Written Opinion.
PCT/US19/20065, May 16, 2019, International Search Report and Written Opinion.
International Search Report and Written Opinion for International Application No. PCT/US2018/063215 dated Mar. 21, 2019.
International Search Report and Written Opinion for International Application No. PCT/US2019/015134 dated May 15, 2019.
International Search Report and Written Opinion for International Application No. PCT/US2019/015167 dated May 21, 2019.
International Search Report and Written Opinion for International Application No. PCT/US2019/015174 dated May 21, 2019.
International Search Report and Written Opinion for International Application No. PCT/US2019/015238 dated May 16, 2019.
International Search Report and Written Opinion for International Application No. PCT/US2019/015183 dated May 3, 2019.
International Search Report and Written Opinion for International Application No. PCT/US2019/015180 dated May 16, 2019.
International Search Report and Written Opinion for International Application No. PCT/US2019/015244 dated May 16, 2019.
International Search Report and Written Opinion for International Application No. PCT/US19/20065 dated May 16, 2019.
Arkenbout et al., Robust Hand Motion Tracking through Data Fusion of 5DT Data Glove and Nimble VR Kinect Camera Measurements. Sensors. 2015;15:31644-71.
Davoodi et al., Development of a Physics-Based Target Shooting Game to Train Amputee Users of Multijoint Upper Limb Protheses. Presence. Massachusetts Institute of Technology. 2012;21(1):85-95.
Favorskaya et al., Localization and Recognition of Dynamic Hand Gestures Based on Hierarchy of Manifold Classifiers. International Archives of the Photogrammetry, Remote Sensing and Spatial Information Sciences. 2015;XL-5/W6:1-8.
Hauschild et al., A Virtual Reality Environment for Designing and Fitting Neural Prosthetic Limbs. IEEE Transactions on Neural Systems and Rehabilitation Engineering. 2007;15(1):9-15.
Lee et al., Motion and Force Estimation System of Human Fingers. Journal of Institute of Control, Robotics and Systems. 2011;17(10):1014-1020.
Lopes et al., Hand/arm gesture segmentation by motion using IMU and EMG sensing. ScienceDirect. Elsevier. Procedia Manufacturing. 2017;11:107-13.
Martin et al., A Novel Approach of Prosthetic Arm Control using Computer Vision, Biosignals, and Motion Capture. IEEE. 2014. 5 pages.
Mendes et al., Sensor Fusion and Smart Sensor in Sports and Biomedical Applications. Sensors. 2016;16(1569):1-31.
Sartori et al., Neural Data-Driven Musculoskeletal Modeling for Personalized Neurorehabilitation Technologies. IEEE Transactions on Biomedical Engineering. 2016;63(5):879-93.
PCT/US2019/028299, Aug. 9, 2019, International Search Report and Written Opinion.
PCT/US2019/034173, Sep. 18, 2019, International Search Report and Written Opinion.
PCT/US2019/031114, Aug. 6, 2019, Invitation to Pay Additional Fees.
Extended European Search Report for European Application No. EP 17835111.0 dated Nov. 21, 2019.
Extended European Search Report for European Application No. EP 17835140.9 dated Nov. 26, 2019.
International Search Report and Written Opinion for International Application No. PCT/US2019/037302 dated Oct. 11, 2019.
International Search Report and Written Opinion for International Application No. PCT/US2019/042579 dated Oct. 31, 2019.
Invitation to Pay Additional Fees for International Application No. PCT/US2019/049094 dated Oct. 24, 2019.
International Search Report and Written Opinion for International Application No. PCT/US2019/052131 dated Dec. 6, 2019.
International Search Report and Written Opinion for International Application No. PCT/US2019/046351 dated Nov. 7, 2019.
Al-Mashhadany, Inverse Kinematics Problem (IKP) of 6-DOF Manipulator Bgy Locally Recurrent Neural Networks (LRNNs). Management and Service Science (MASS). 2010 International Conference ON, IEEE. Aug. 24, 2010. 5 pages. ISBN: 978-1-4244-5325-2.
Kipke et al., Silicon-substrate Intracortical Microelectrode Arrays for Long-Term Recording of Neuronal Spike Activity in Cerebral Cortex. IEEE Transactions on Neural Systems and Rehabilitation Engineering. 2003;11(2):151-155.
Marcard et al., Sparse Inertial Poser: Automatic 3D Human Pose Estimation from Sparse IMUs. Eurographics. 2017;36(2). 12 pages.
Mohamed, Homogeneous cognitive based biometrics for static authentication. Dissertation submitted to University of Victoria, Canada. 2010. 149 pages. URL:http://hdl.handle.net/1828/3211 [last accessed Oct. 11, 2019].
Wittevrongel et al., Spatiotemporal Beamforming: A Transparent and Unified Decoding Approach to Synchronous Visual Brain-Computer Interfacing. Frontiers in Neuroscience. 2017;11:1-12.
Zacharaki et al., Spike pattern recognition by supervised classification in low dimensional embedding space. Brain Informatics. 2016;3:73-8. DOI: 10.1007/s40708-016-0044-4.
International Search Report and Written Opinion for International Application No. PCT/US2019/015180 dated May 28, 2019.
International Search Report and Written Opinion for International Application No. PCT/US2019/028299 dated Aug. 9, 2019.
Invitation to Pay Additional Fees for International Application No. PCT/US2019/031114 dated Aug. 6, 2019.
International Search Report and Written Opinion for International Application No. PCT/US2019/034173 dated Sep. 18, 2019.
Gopura et al., A Human Forearm and wrist motion assist exoskeleton robot with EMG-based fuzzy-neuro control. Proceedings of the 2nd IEEE/RAS-EMBS International Conference on Biomedical Robotics and Biomechatronics. Oct. 19-22, 2008. 6 pages.
Valero-Cuevas et al., Computational Models for Neuromuscular Function. NIH Public Access Author Manuscript. Jun. 16, 2011. 52 pages.

(56) References Cited

OTHER PUBLICATIONS

Yang et al., Surface EMG based handgrip force predictions using gene expression programming. Neurocomputing. 2016;207:568-579.
EP 17835111.0, Nov. 21, 2019, Extended European Search Report.
EP 17835140.9, Nov. 26, 2019, Extended European Search Report.
PCT/US2019/037302, Oct. 11, 2019, International Search Report and Written Opinion.
PCT/US2019/042579, Oct. 31, 2019, International Search Report and Written Opinion.
PCT/US2019/046351, Nov. 7, 2019, International Search Report and Written Opinion.
PCT/US2019/049094, Oct. 24, 2019, Invitation to Pay Additional Fees.
PCT/US2019/052131, Dec. 6, 2019, International Search Report and Written Opinion.

* cited by examiner

SYSTEM AND METHOD FOR MEASURING THE MOVEMENTS OF ARTICULATED RIGID BODIES

CROSS-REFERENCE TO RELATED APPLICATIONS

This application claims the benefit under 35 U.S.C. § 119(e) of U.S. Provisional Patent Application Ser. No. 62/366,426, filed Jul. 25, 2016, and entitled "SYSTEM FOR MEASURING THE MOVEMENTS OF MULTIPLE ARTICULATED RIGID BODIES," the entire contents of which is incorporated by reference herein.

BACKGROUND

In some computer applications that generate musculoskeletal representations of the human body, it is desirable for the application to know the spatial positioning, orientation and movement of a user's body to provide a realistic representation of body movement. For example, in a virtual reality (VR) environment, tracking the spatial position of the user's hand enables the application to represent the hand motion in the VR environment, which allows the user to interact with (e.g., by grasping or manipulating) virtual objects within the VR environment. Some existing techniques for tracking movements using wearable sensors include using information obtained from multiple Inertial Measurement Units (IMUs) affixed to different parts of the user's body, and using external imaging devices (e.g., fixed-position cameras) to reconstruct the position and orientation of parts of the user's body.

SUMMARY

Some embodiments are directed to predicting information about the positioning and movements of portions of a user's body (e.g., a user's arm, hand, leg, etc.) represented as multi-segment articulated rigid body system in an autonomous manner, i.e., without requiring external sensors, such as cameras, lasers, or global positioning systems (GPS), and also without requiring sensors (e.g., inertial measurement units (IMUs)) to be positioned on each segment of the user's body.

Signals recorded by wearable autonomous sensors placed at locations on the user's body are provided as input to a statistical model trained to generate spatial information (e.g., position of, orientation of, joint angles between) for rigid segments of a multi-segment articulated rigid body model of the human body. As a result of the training, the statistical model implicitly represents the statistics of motion of the articulated rigid body under defined movement constraints. The output of the trained statistical model may in turn be used for applications such as rendering a representation of the user's body in a virtual environment, interaction with physical or virtual objects, and monitoring a user's movements as the user performs a physical activity to assess, for example, whether the user is providing the physical activity in a desired manner.

In some embodiments, movement data obtained by a single movement sensor positioned on a user (e.g., a user's wrist) may be provided as input (e.g., raw or after pre-processing) to a trained statistical model. Corresponding output generated by the trained statistical model may be used to determine spatial information for one or more segments of a multi-segment articulated rigid body model for the user. For example, the output may be used to determine the position and/or orientation of one or more segments in the multi-segment articulated rigid body model. As another example, the output may be used to determine angles between connected segments in the multi-segment articulated rigid body model.

Some embodiments provide for a computerized system for determining spatial information for a multi-segment articulated rigid body system having at least an anchored segment and a non-anchored segment connected to the anchored segment, each segment in the multi-segment articulated rigid body system representing a respective body part of a user. The computerized system comprises: a first autonomous movement sensor; at least one computer hardware processor; and at least one non-transitory computer-readable storage medium storing processor-executable instructions that, when executed by the at least one computer hardware processor, cause the at least one computer hardware processor to perform: obtaining signals recorded by the first autonomous movement sensor when the first movement sensor is coupled to a body part of the user represented by the non-anchored segment; providing the obtained signals as input to a trained statistical model and obtaining corresponding output of the trained statistical model; and determining, based on the corresponding output of the trained statistical model, spatial information for at least the non-anchored segment of the multi-segment articulated rigid body system. The spatial information may include position information for the non-anchored segment relative to an anchor point of the anchored segment and/or relative to any other suitable reference frame.

Some embodiments provide for a method for determining spatial information for a multi-segment articulated rigid body system having at least an anchored segment and a non-anchored segment connected to the anchored segment, each segment in the multi-segment articulated rigid body system representing a respective body part of a user, the method comprising: obtaining signals recorded by a first autonomous movement sensor when the first autonomous movement sensor is coupled to a body part of the user represented by the non-anchored segment; providing the obtained signals as input to a trained statistical model and obtaining corresponding output of the trained statistical model; and determining, based on the corresponding output of the trained statistical model, spatial information for at least the non-anchored segment of the multi-segment articulated rigid body system.

Some embodiments provide for at least one non-transitory computer-readable storage medium storing processor executable instructions that, when executed by a computer hardware processor, cause the computer hardware processor to perform a method for determining spatial information for a multi-segment articulated rigid body system having at least an anchored segment and a non-anchored segment connected to the anchored segment, each segment in the multi-segment articulated rigid body system representing a respective body part of a user. The method comprises: obtaining signals recorded by a first autonomous movement sensor when the first autonomous movement sensor is coupled to a body part of the user represented by the non-anchored segment; providing the obtained signals as input to a trained statistical model and obtaining corresponding output of the trained statistical model; and determining, based on the corresponding output of the trained statistical model, spatial information for at least the non-anchored segment of the multi-segment articulated rigid body system.

In some embodiments, including any of the preceding embodiments, the anchored segment is anchored to an anchor point, and determining the spatial information for at least the non-anchored segment comprises: determining the position of the non-anchored segment relative to the anchor point.

In some embodiments, including any of the preceding embodiments, the anchored segment is anchored to an anchor point, and determining the spatial information for at least the non-anchored segment comprises: determining a spatial relationship between the anchored segment and the non-anchored segment.

In some embodiments, including any of the preceding embodiments, determining the spatial relationship between the anchored segment and the non-anchored segment comprises: determining a set of one or more joint angles describing the spatial relationship between the anchored segment and the non-anchored segment.

In some embodiments, including any of the preceding embodiments, the first autonomous movement sensor comprises an inertial measurement unit (IMU).

In some embodiments, including any of the preceding embodiments, the first autonomous movement sensor comprises at least one sensor selected from the group consisting of a gyroscope, an accelerometer, and a magnetometer.

In some embodiments, including any of the preceding embodiments, the trained statistical model comprises a trained non-linear regression model. In some embodiments, including any of the preceding embodiments, the trained statistical model comprises a trained recurrent neural network. In some embodiments, including any of the preceding embodiments, the trained statistical model comprises a trained variational autoencoder.

In some embodiments, including any of the preceding embodiments, the first movement sensor is arranged on a single wearable device configured to be worn on or around a body part of the user.

In some embodiments, including any of the preceding embodiments, the single wearable device comprises a flexible or elastic band configured to be worn around the body part of the user.

In some embodiments, including any of the preceding embodiments, the processor-executable instructions, when executed by the at least one computer hardware processor, further cause the at least one computer hardware processor to perform: sending one or more control signals to a controller configured to instruct a device to perform an action based on the one or more control signals.

In some embodiments, including any of the preceding embodiments, the processor-executable instructions, when executed by the at least one computer hardware processor, further cause the at least one computer hardware processor to perform executing a computer application that provides a virtual reality environment, the controller comprises a display controller configured to instruct a display to display a visual representation of a character in the virtual reality environment, and the one or more control signals comprise signals to instruct the display controller to update in real time the visual representation of the character based, at least in part, on the determined spatial information.

In some embodiments, including any of the preceding embodiments, the virtual reality environment comprises a virtual object and updating the visual representation of the character based on the determined spatial information comprises updating the visual representation such that the character interacts with the virtual object.

In some embodiments, including any of the preceding embodiments, interacting with the virtual object comprises an action selected from the group consisting of grasping the virtual object, dropping the virtual object, pushing the virtual object, throwing the virtual object, pulling the virtual object, opening the virtual object, and closing the virtual object.

In some embodiments, including any of the preceding embodiments, the controller includes a control interface for a physical device, and wherein the one or more control signals comprise signals to instruct at least one component of the physical device to move based on the determined spatial information.

In some embodiments, including any of the preceding embodiments, the processor-executable instructions, when executed by the at least one computer hardware processor, further cause the at least one computer hardware processor to perform: updating a computer-generated representation of the multi-segment articulated rigid body system based, at least in part, on the determined spatial information; and storing, on the at least one non-transitory computer-readable storage medium, the updated computer-generated representation of the multi-segment articulated rigid body system.

Some embodiments provide a computerized system for training a statistical model for generating spatial information for a multi-segment articulated rigid body system having at least an anchored segment and a non-anchored segment connected to the anchored segment, each segment in the multi-segment articulated rigid body system representing a respective body part of a user, the computerized system comprising: a plurality of autonomous movement sensors; at least one computer hardware processor; and at least one non-transitory computer-readable storage medium storing processor-executable instructions that, when executed by the at least one computer hardware processor, causes the at least one computer hardware processor to perform: obtaining movement signals recorded by the plurality of autonomous movement sensors when each of the plurality of autonomous movement sensors is coupled to a body part of a first user represented by a respective segment in the multi-segment articulated rigid body system; generating training data using the obtained movement signals; training the statistical model using at least some of the generated training data to output a trained statistical model, wherein the trained statistical model is configured to generate spatial information for a multi-segment articulated rigid body system using movement signals obtained by a single autonomous movement sensor coupled to a body part of a second user; and storing the trained statistical model.

Some embodiments provide a method for training a statistical model for generating spatial information for a multi-segment articulated rigid body system having at least an anchored segment and a non-anchored segment connected to the anchored segment, each segment in the multi-segment articulated rigid body system representing a respective body part of a user, the method comprising: obtaining movement signals recorded by a plurality of autonomous movement sensors when each of the plurality of autonomous movement sensors is coupled to a body part of a first user represented by a respective segment in the multi-segment articulated rigid body system; generating training data using the obtained movement signals; training the statistical model using at least some of the generated training data to output a trained statistical model, wherein the trained statistical model is configured to generate spatial information for a multi-segment articulated rigid body system using movement signals obtained by a single autonomous movement sensor coupled to a body part of a second user; and storing the trained statistical model.

Some embodiments provide for at least one non-transitory computer-readable storage medium storing processor executable instructions that, when executed by a computer hardware processor, cause the computer hardware processor to perform a method for training a statistical model for generating spatial information for a multi-segment articulated rigid body system having at least an anchored segment and a non-anchored segment connected to the anchored segment, each segment in the multi-segment articulated rigid body system representing a respective body part of a user, the method comprising: obtaining movement signals recorded by a plurality of autonomous movement sensors when each of the plurality of autonomous movement sensors is coupled to a body part of a first user represented by a respective segment in the multi-segment articulated rigid body system; generating training data using the obtained movement signals; training the statistical model using at least some of the generated training data to output a trained statistical model, wherein the trained statistical model is configured to generate spatial information for a multi-segment articulated rigid body system using movement signals obtained by a single autonomous movement sensor coupled to a body part of a second user; and storing the trained statistical model on the at least one non-transitory storage medium.

In some embodiments, including any of the preceding embodiments, the first user and the second user are a same user.

In some embodiments, a statistical model may be trained, for example using tracking actual movement data measured from the articulated rigid body system, as that system may be constrained by certain physical (e.g., range of motion) and other constraints. As a result, the trained statistical model implicitly represents the statistics of motion of the articulated rigid body under the defined constraints. Once the model has learned the statistics of motion, real-time motion data (e.g., as received from a wrist-worn IMU) may be provided as input to the model. A computational system using the approach may determine the likely position and orientation of the articulated rigid body segment (e.g., the user's wrist) relative to a reference frame, without requiring sensors on one or more other segments (e.g., the user's upper arm), and without requiring use of external devices or supplemental position information. With respect to a user, the reference frame may be defined by the user's torso and the anchor point, e.g., the user's shoulder. The output from the trained statistical model represents a computationally-determined position and orientation of the rigid body segment of interest relative to the reference frame, and this output can then be used for many applications, such as rendering, interaction with virtual objects, or the like.

The computational approach of this disclosure preferably takes advantage of the constraints and statistical patterns under which the articulated rigid body system moves. The constraints are physical in nature (such as the user's arm is physically attached to the user's body thereby limiting its range of motion), and they can be either explicitly imposed in the construction of the model or learned from the data along with the statistical patterns of movement. The statistical patterns of movement arise from behavioral tendencies. An example of such a pattern may be that a pair of body elements is more often positioned at an angle to one another, as opposed to straight up and down. These statistical patterns can be imposed as explicit statistical priors or regularizations, or they can be implicitly captured in the model parameters learned from training data.

In a preferred but non-limiting embodiment, the technique uses a statistical model to computationally determine the relative (to the given reference frame) position and orientation of a segment of the articulated rigid body system operating under such constraints.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF DRAWINGS

Various non-limiting embodiments of the technology will be described with reference to the following figures. It should be appreciated that the figures are not necessarily drawn to scale.

DETAILED DESCRIPTION

Figure 1:
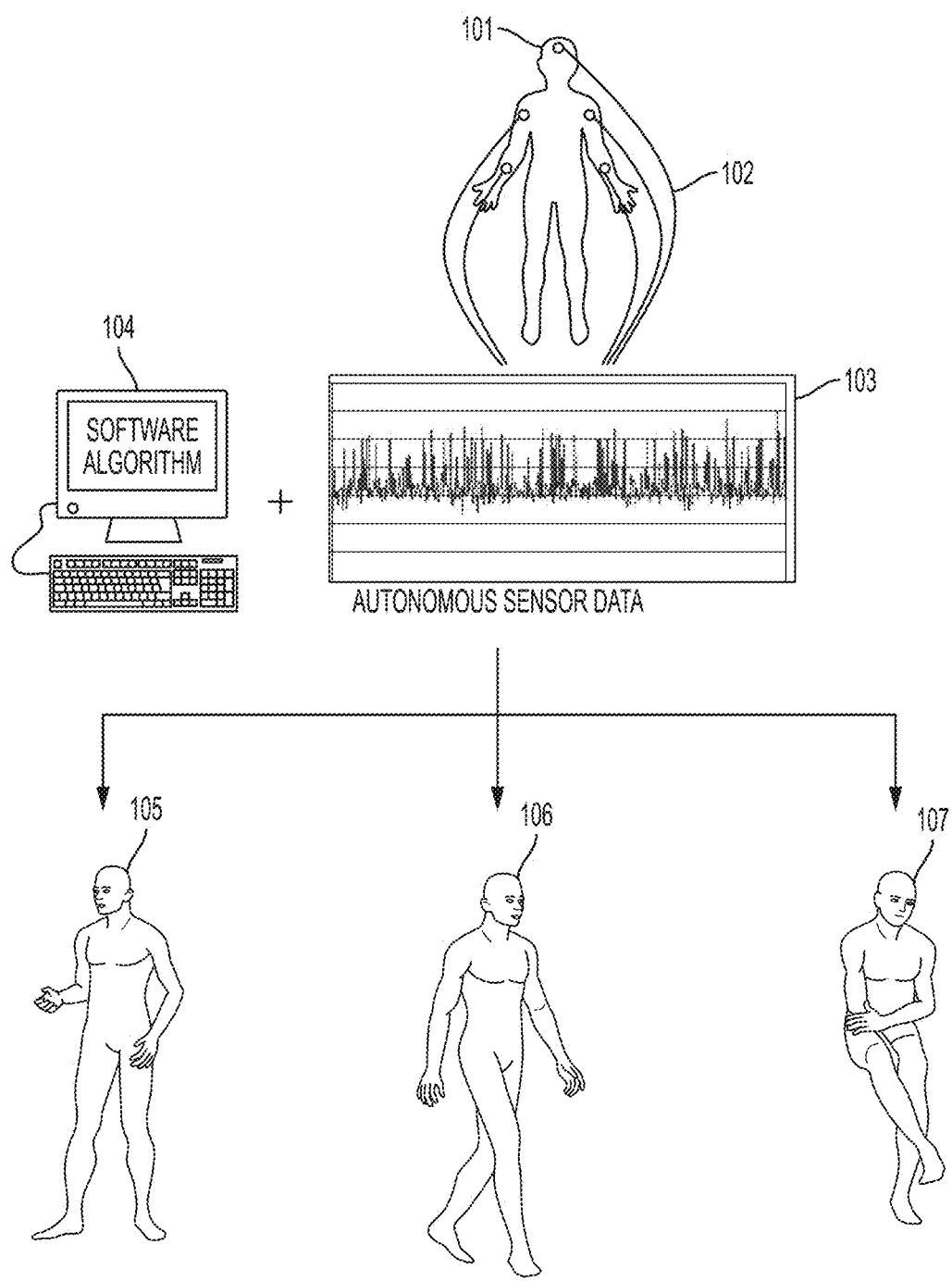
FIG. 1 depicts how IMU data is captured for a training phase in accordance with some embodiments of the technology described herein.

The human musculo-skeletal system can be modeled as a multi-segment articulated rigid body system, with joints forming the interfaces between the different segments and joint angles defining the spatial relationships between connected segments in the model. Constraints on the movement at the joints are governed by the type of joint connecting the segments and the biological structures (e.g., muscles, tendons, ligaments) that restrict the range of movement at the joint. For example, the shoulder joint connecting the upper arm to the torso and the hip joint connecting the upper leg to the torso are ball and socket joints that permit extension and flexion movements as well as rotational movements. By contrast, the elbow joint connecting the upper arm and the forearm and the knee joint connecting the upper leg and the lower leg allow for a more limited range of motion.

In kinematics, rigid bodies are objects that exhibit various attributes of motion (e.g., position, orientation, angular velocity, acceleration). Knowing the motion attributes of one segment of the rigid body enables the motion attributes for other segments of the rigid body to be determined based on constraints in how the segments are connected. For example, the arm may be modeled as a two-segment articulated rigid body with an upper portion corresponding to the upper arm connected at a shoulder joint to the torso of the body and a lower portion corresponding to the forearm, wherein the two segments are connected at the elbow joint. Considering the shoulder as an anchor point of the two-segment articulated rigid body, the segment representing the upper arm is considered "anchored" and the segment corresponding to the lower arm is considered "un-anchored." As another example, the hand may be modeled as a multi-segment articulated body with the joints in the wrist and each finger forming the interfaces between the multiple segments in the model. In some embodiments, movements of the segments in the rigid body model can be simulated as an articulated rigid body system in which orientation and position information of a segment relative to other segments in the model are predicted using a trained statistical model, as described in more detail below.

As described herein, a multi-segment articulated rigid body system is used to model the human musculo-skeletal system. However, it should be appreciated that some segments of the human musculo-skeletal system (e.g., the forearm), though approximated as a rigid body in the articulated rigid body system, may include multiple rigid structures (e.g., the ulna and radius bones of the forearm) that provide for more complex movement within the segment that is not explicitly considered by the rigid body model. Accordingly, a model of an articulated rigid body system for use with some embodiments of the technology described herein may include segments that represent a combination of body parts that are not strictly rigid bodies.

Some embodiments of the techniques described herein enable a computing system to determine time-varying orientation and position of the non-anchored segment relative to the anchored point on the first segment, e.g., to determine a configuration of the articulated rigid body system during the user's real-time movements (e.g., an interaction with an application such as a virtual reality game). In some embodiments, during the real-time movement tracking, just information sensed from a wrist-attached IMU may be used. More generally, techniques described herein allow for reconstruction of human movements from a small number of movement sensors. For example, some embodiments provide for techniques that allow for determining the position and/or orientation of both the forearm and upper arm relative to the torso reference frame using a single wrist-worn device, and without external devices or sensors.

As additional background, typically there are constraints and statistical patterns under which the articulated rigid body moves. The constraints under which the articulated rigid body moves are mechanical in nature (such as the user's arm is physically attached to the user's body thereby limiting its range of motion), and they can be either explicitly imposed in the construction of a statistical model, or they may be learned from the data along with statistical patterns of movement. The statistical patterns of movement typically arise from behavioral tendencies. An example of such a pattern may be that a pair of body elements is more often positioned at an angle to one another, as opposed to straight up and down. These statistical patterns can be imposed as explicit statistical priors or regularizations, or they can be implicitly captured in the model parameters learned from training data.

Generalizing, the articulated rigid body system (and any movement sensor attached thereto) thus can be said to be operating in a constrained manner, or under a set of one or more constraints. As will be described, the techniques described herein provide an approach that may be used to reconstruct spatial information of one or more segments of the multi-segment articulated rigid body system operating under such constraints. The spatial information may indicate position (e.g., in 3D space) of one or more segments, orientation of one or more segments, and/or angles between one or more pairs of connected segments, and/or any other suitable information about the spatial location of the segment(s) of the articulated rigid body system. The spatial position may be provided in any suitable reference frame including, by way of example, the torso relative frame (e.g., the reference frame defined by the user's torso). In some embodiments, the techniques described herein are used to train statistical models that leverage the existence of these constraints to facilitate generation of the movement data that models a non-anchored segment's relative position and orientation in 3D space. In some embodiments, the trained statistical models may represent these constraints through their parameters.

FIG. 1 depicts an illustrative approach, in accordance with some embodiments. In this example, and during a learning phase, a subject (101) is connected to one or more autonomous sensors (102), which sense the subject's movements and provide data from which the configuration dynamics of the subject can be generated. In some embodiments, the autonomous sensors 102 may be IMUs that are positioned on the user's upper arm and forearm, and perhaps elsewhere. The measurement data (103) is processed using algorithms (104) to reconstruct the relative position and orientation of the subject, as seen in 105, 106, and 107 in FIG. 1. As will be described, the anatomy of particular interest here is the user's wrist, as a typical (but non-limiting) use case involves an application (such as virtual reality game) in which it is desired to computationally determine a relative position and orientation of the user's hand, e.g., to facilitate rendering and display of the user's hand in a VR simulation.

In some embodiments, an IMU may provide a set of measurement data d(t), such as acceleration over time a(t), angular velocity over time w(t), and/or sensed magnetic field over time m(t). This information may be collected by the IMU component sensors, and the IMU may output that data individually or collectively. A sensor fusion algorithm may be used to process the sensed data in order to compute additional derived measurements, such as orientation over time q(t). Thus, the IMU accumulates such data over time as a time-series. From these time-series data, the time-varying state of the rigid body may be determined by these measurements.

In some embodiments, a statistical model of the articulated rigid body system motion may be built using training data. The training data may be derived from the user whose movements are desired to be determined, from arm movements measured from one or more other users, by executing a "simulation" of movements of such a system, by augmenting data obtained from an actual user with data derived from a simulation, or combinations thereof. Depending on how the training data is to be captured or generated, one or more auxiliary devices or systems (e.g., a motion capture system, a laser scanner, a device to measure mutual magnetic induction, etc.) may be used. The statistical model may be generated in a pre-processing or off-line training phase. As a result of the training, the model implicitly represents the statistics of motion of the articulated rigid body system under the defined constraints, and the relationship between movement trajectories and IMU measurement time series. After the statistical model is built in the training phase, it is then used to facilitate a real-time (or substantially real-time) data analysis to determine computationally the relative position and orientation of the user's wrist. During the real-time data analysis phase, preferably an IMU is used only on the user's forearm. In use, real-time motion data (received from a user's wrist-worn IMU) is fed to the statistical model to enable the computing system to computationally know the relative position and orientation of the rigid body segment of interest.

Thus, in some embodiments, during a learning phase, an IMU is positioned, e.g., on an end of the user's forearm, herein referred to as the "wrist". Because the user's forearm is a segment of the multi-segment articulated body system, the IMU may be positioned anywhere on the forearm (segment). When the training data is generated using human user(s), an IMU also is positioned on the user's upper arm. As noted above, however, the training data may be generated in other ways, such as synthetically or semi-synthetically. In turn, a statistical model (e.g., a recurrent neural network, a variational autoencoder, etc.) may be trained using the training data. In some embodiments, the time-series data generated by the one or more IMUs may be used to train the statistical model from which estimates of the user's wrist position and orientation (and potentially the degree of uncertainty about the estimates) at a given time can be made or derived. In some embodiments, the statistical model may provide estimates of time-varying orientations and positions of the segments of a two-segment articulated rigid body, wherein one of the segments is anchored at one point to fix its position but not its orientation. The statistical model may be generated in a pre-processing or off-line training phase. In this manner, the user's real biophysical data is used to train the model. As a result of the training, the statistical model may implicitly represents the statistics of motion of the articulated rigid body under the defined constraints, and the relationship between movement trajectories and IMU measurement time series.

In some embodiments, the statistical model may be a long short-term memory (LSTM) recurrent neural network that is trained using the biophysical data sensed from the one or more IMU devices worn by the user as depicted in FIG. 1. An LSTM may include a set of recurrently connected memory units that can persist information over extended numbers of update cycles. In a recurrent neural network, the connections within the network may form a directed cycle. This may create an internal network state that allows it to exhibit dynamic temporal behavior. Recurrent neural networks use their internal memory to process sequences of input having any suitable length. In some embodiments, an LSTM may be trained using gradient descent and back-propagation through time. In some embodiments, a number of LSTM RNN layers may be stacked together and trained to find connection parameters that maximize a probability of some output sequences in a training set, given the corresponding input sequences.

In some embodiments, a neural network model may be trained using mechanical motion data and, as noted above, the model may represent, implicitly, movement statistics and constraints due to the articulation of the user's arm relative to his or her torso, and the relation of the movements to the measured data. These movement statistics and relations to measurement data may be encoded in the values of the neural network model parameters (e.g., LSTM weights) that were obtained during training. In some embodiments, the statistical model may be trained and subsequently used without any external reference data (e.g., GPS data, captured image data, laser and other ranging information, etc.), for example by training a variational auto-encoder with a generative model. However, in other embodiments, the statistical model may be trained by using such external reference data.

In some embodiments, after the statistical model has been trained (during the learning phase), it may be used to determine (computationally) the relative position and orientation of a rigid body segment (e.g., as that segment interacts with the application of interest). For example, after the statistical model is trained, new movement data may be captured from the user's wrist-worn IMU (e.g., as the user interacts with a virtual reality application). The new movement data may represent movement of the user's forearm (represented by a non-anchored segment in a multi-segment articulated rigid body system). The new movement data may be provided as input to the trained statistical model and corresponding output may be obtained. The output may indicate the position and/or orientation of the user's forearm (represented by the non-anchored segment), the position and/or orientation of the user's upper arm (represented, in the articulated rigid body system by an anchored segment coupled to the non-anchored segment representing the forearm), information indicating the relative positions of the user's forearm and upper arm (e.g., by outputting a set of joint angles between the forearm and upper arm), and/or any other spatial information indicating how the user's arm may be situated in 3D space. In some embodiments, the output may indicate such spatial information directly (i.e., the spatial information may be provided as the actual output of the trained statistical model). In other embodiments, the output may indicate such spatial information indirectly (i.e., the spatial information may be derived from the output of the trained statistical model).

In some embodiments, the spatial information indicated by the output of the trained statistical model may be indicated with reference to a certain reference frame, for example, the torso reference frame of the user, the reference frame of the room in which the user is located, etc. In some embodiments, the anchored segment in the multi-segment articulated rigid body model may be attached to an anchor point (which may represent the user's shoulder, for example) and the spatial information indicated by the output of the trained statistical model may be indicated relative to the anchor point.

Figure 2:
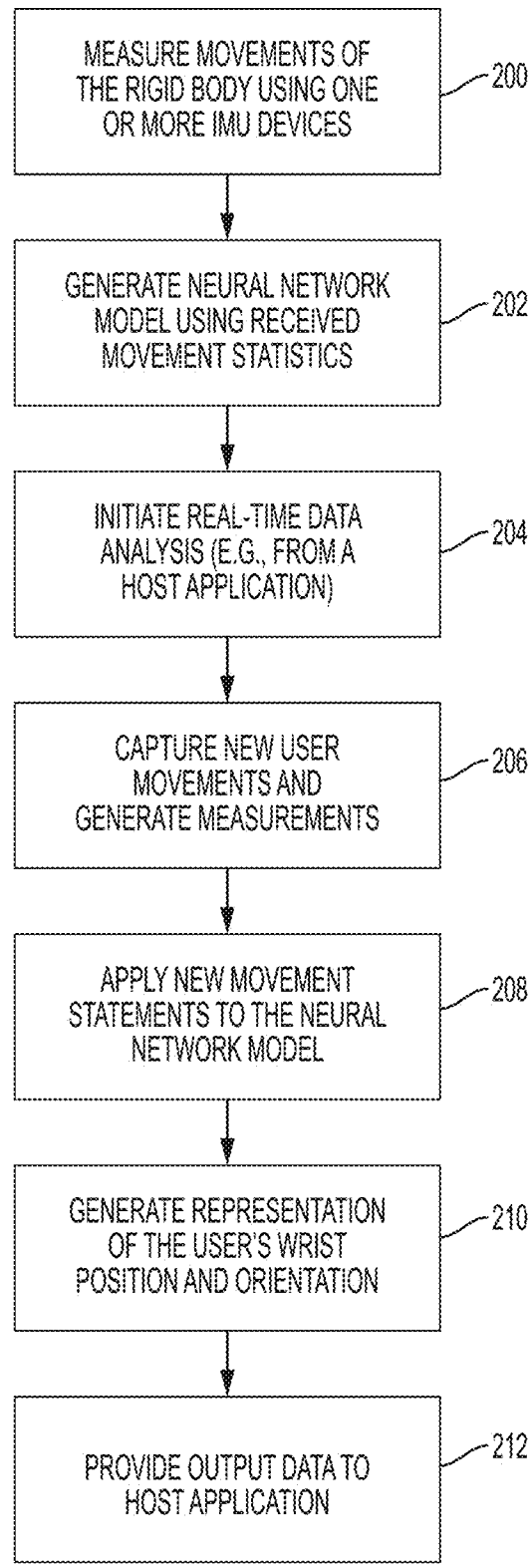
FIG. 2 is a flowchart of an illustrative process for generating and using a statistical model of user movement, in accordance with some embodiments of the technology described herein.

FIG. 2 is a flowchart of an illustrative process for generating and using a statistical model of user movement, in accordance with some embodiments of the technology described herein. This process may be implemented using any suitable computing device(s), as aspects of the technology described herein are not limited in this respect. At step 200, the movements of the multi-segment articulated rigid body system (e.g., the user's arm) are measured, for example, using multiple IMU devices. At step 202, and during the learning phase, a statistical model may be trained using the data collected by the multiple IMU devices. Thereafter, at step 204, the real-time data analysis phase is initiated. In the real-time data analysis phase, a user wears an IMU on his or her wrist (or anywhere else on the forearm). New measurements are then captured by the user-worn IMU at step 206. At step 208, this new measurement data is applied to the trained statistical model. Based on the trained model, data representing an estimate of the position of the non-anchored segment relative to an anchor point of an anchored segment (namely, the user's upper arm that does not carry an IMU) is computed at step 210. At step 212, results of the computation may be provided to a host application (e.g., a virtual reality application or any other suitable application) to facilitate an operation associated with the application.

Figure 3:
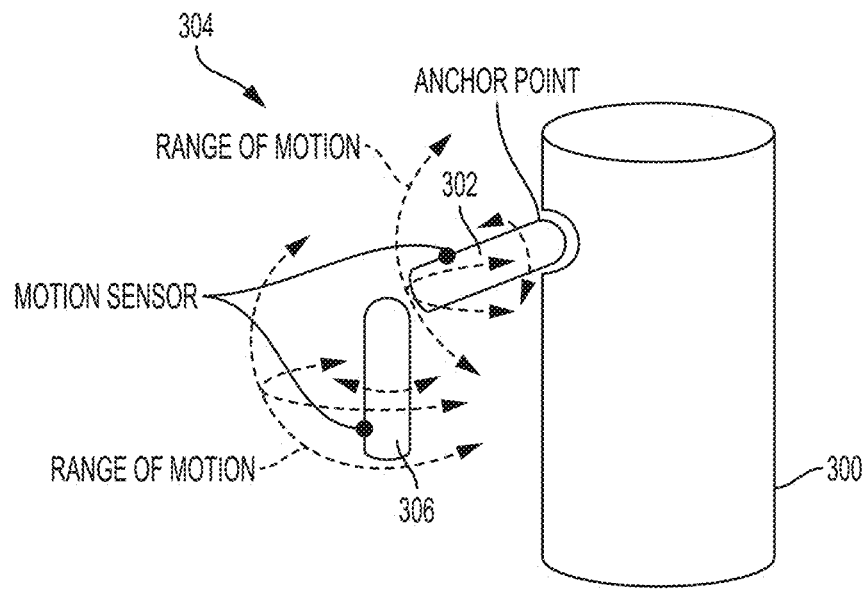
FIG. 3 illustrates a multi-segment articulated rigid body system, in accordance with some embodiments described herein.

FIG. 3 depicts a model of the multi-segment articulated rigid body system as described above. In this embodiment, the system comprises a rigid form 300 representing the human torso, the first segment 302 corresponding to the upper arm attached to the form 300 at the anchor point 304 (a ball-in-socket joint), and the second segment 306 corresponding to the user's forearm. Movement sensors 308 are attached to each of the first and second segments, and the range of motion for each segment also is shown. In this illustrative embodiment, the forearm has two degrees of freedom.

There is no limit or restriction on the use that may be made of the computation. Generalizing, the approach generates or obtains the statistical model that has learned the statistics of motion and their relation to measurements. The statistical model is then used during real-time data analysis on new motion data received by the computing system and representing motion of an articulated rigid body segment of interest; in particular, the computing system uses the statistical model to determine the position and orientation of the segment of the articulated rigid body.

One non-limiting use case of the approach described above is for rendering. To this end, there are well-known computer-implemented rendering techniques that computationally-render a user's hands and wrists, e.g., when the user puts on a VR headband. More specifically, and in connection with the user's interaction with the host application of this type, it is desired to generate a digital representation of the user's wrist position and orientation in 3D space. In the approach herein, this digital representation of the user's wrist position and orientation in effect is computed (predicted) by the model in real-time using only IMU data measured from movement of the one rigid body segment to which the IMU is attached. Thus, in an example use case, once a statistical model (e.g., a neural network) has been trained to implicitly learn the movement statistics and their relation to measurements (as they are encoded in its weight parameters), during the real-time data analysis phase, IMU information sensed from just the user's forearm is used by the neural network to predict the user's arm movement. Stated another way, when interacting with the application, the measured or sensed movement of the lower segment of the multi-segment articulated rigid body system may be used to predict the movement of that segment relative to the anchor point. With the resulting prediction, the application knows the absolute orientation and position of the user's wrist and hand relative to the user's torso, and it can then respond appropriately to the user's actions or commands depending on the nature and operation of the application.

The notion of a computing machine model implicitly learning the statistics of motion may be conceptualized as follows. In particular, the statistical model of the user's movements that is generated during the training phase provides an estimate of where the user's wrist is at a given time. Position estimates from integration of the IMU measurement data, while generally useful, may drift over time due to accumulation of noise. In the approach herein, however, the articulation constraints in the statistical model may counteract the accumulation of noise because accumulated drift results in movement trajectories that are incompatible with the constraints.

In some embodiments, the training data used to estimate parameters of the statistical model may be obtained from a single user or multiple users. In some embodiments, the training data may include training data obtained from a single user and the trained statistical model may be applied to generating spatial information for the same single user. In other embodiments, a statistical model applied to generating spatial information for a particular user may be trained using training data collected from one or more other users, in addition to or instead of the particular user.

In some embodiments, the techniques described herein may be used for controlling a virtual reality gaming application. However, the techniques described herein may be applied to controlling other virtual reality environments, augmented reality environments, remote device, computers, and/or any other suitable physical or virtual device, as aspects of the technology described herein are not limited in this respect.

Although not required, during both the learning and application-interaction phases, the sensed IMU data may be pre-processed in various ways, such as coordinate transformations to remove orientation-specific artifacts and to provide rotational invariance to the biophysical data. Other pre-processing may include signal filtering, and the like.

In some embodiments, the statistical model may be a recurrent neural network (e.g., an LSTM). However, in other embodiments, the statistical model may be a variational autoencoder, a non-linear regression model or any other suitable type of statistical model.

More generally, and for a multi-segment articulated rigid body system with up to n segments, the techniques described herein may be used to predict the position and/or orientation of multiple rigid body segments from information captured from sensors placed on only a subset (e.g., one) of the multiple segments. Thus, in one embodiment, for the human arm consisting of two segments, the techniques described herein may be used to determine positions and/or orientations of both the user's upper arm and forearm from movement information captured from only a single IMU coupled to the user's forearm.

Figure 4:
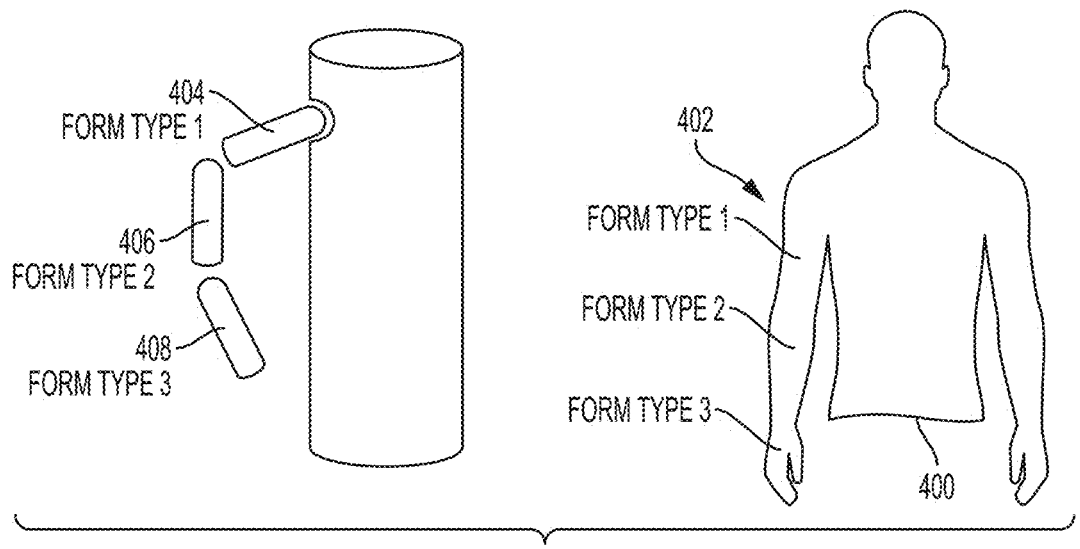
FIG. 4 illustrates a multi-segment rigid body system comprising segments corresponding to body parts of a user, in accordance with some embodiments described herein.
Figure 5:
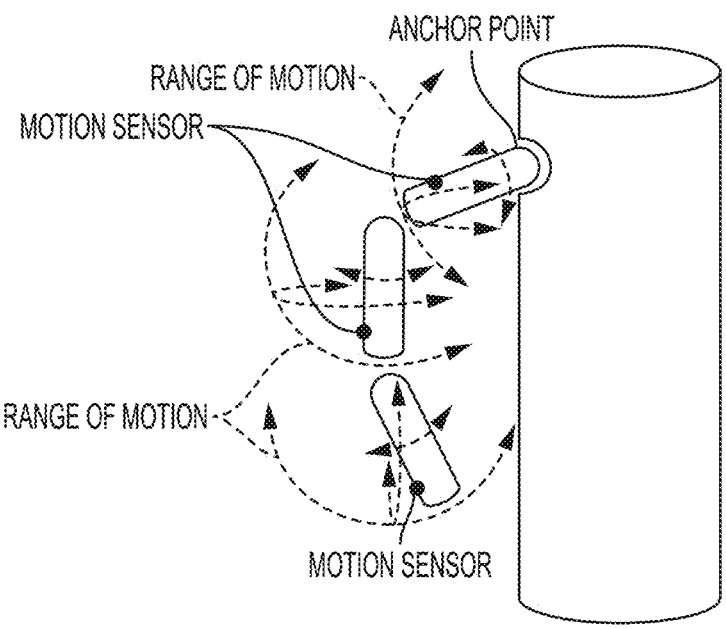
FIG. 5 depicts the various range of motion of each of the segments shown in FIG. 4, in accordance with some embodiments of the technology described herein.

FIG. 4 depicts a multi-segment articulated rigid body system with more than two segments. Like FIG. 3, this drawing again demonstrates how the human arm (in this case including the user's hand) is a segmented form fixed at the shoulder. In particular, as shown here the human torso 400 and the user's right arm 402 are represented by three (3) rigid forms 404, 406 and 408 (each of a distinct type as indicated) corresponding to the user's upper arm, forearm, and hand. FIG. 5 depicts this rigid body system and the range of motion of each segment.

Figure 6:
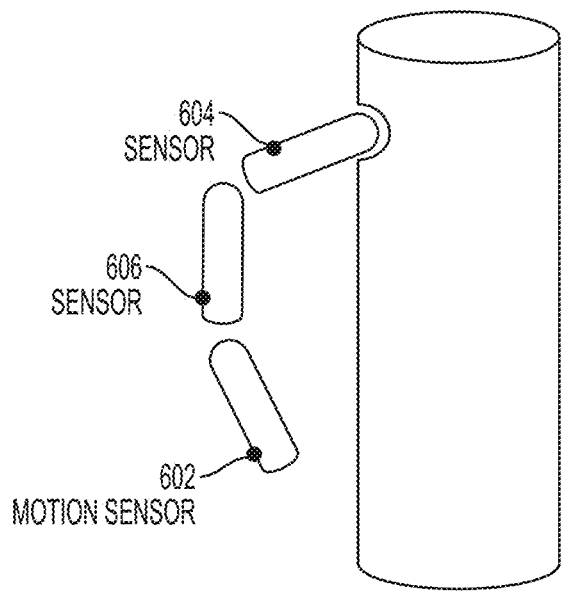
FIG. 6 depicts how movement sensors may be positioned on each segment to capture movement, in accordance with some embodiments of the technology described herein.

FIG. 6 depicts how movement sensors may be positioned on each segment to capture a user's movements, in some embodiments. As shown in FIG. 6, the movement sensor 602 may be an autonomous movement sensor, while the sensors 604 and 606 may be autonomous movement sensors and/or non-autonomous position sensors. In the latter case, an auxiliary motion tracking sub-system may be used during the training phase. Data collected by the movement sensors 602, 604, and 606 may be used to train a statistical model for generating spatial information for segments in a multi-segment articulated rigid body system. For example, the signals obtained by the sensor 602 may be provided as inputs (with or without pre-processing) to a statistical model being trained and signals generated by sensors 604 and 606 may be used to generate corresponding target outputs that the statistical model is to produce in response to application of the inputs. Such data sets comprising inputs (obtained or derived from measurements made by sensor 602) and corresponding outputs (obtained or derived from measurements made by sensors 604 and 606) may be used to train a statistical model in accordance with some embodiments.

Figure 7:
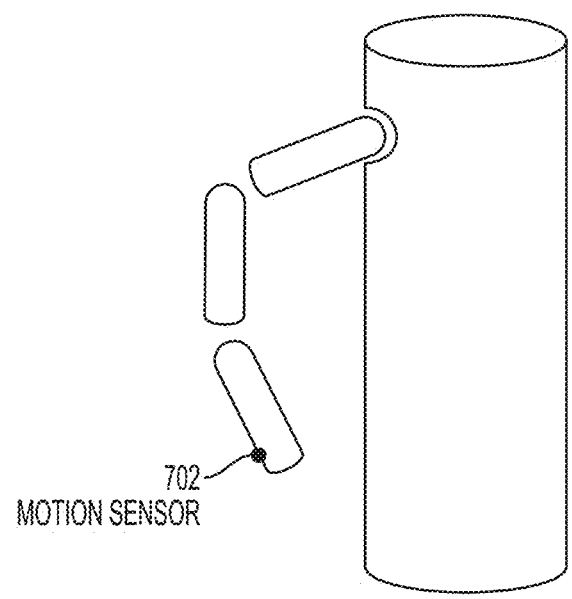
FIG. 7 illustrates an embodiment where measurements obtained by a smaller number of sensors than segments in an articulated rigid body system may be used in conjunction with a trained statistical model to generate spatial information, in accordance with some embodiments of the technology described herein.

FIG. 7 depicts an embodiment in which a single autonomous movement sensor 702 is coupled to a lower segment. Measurements obtained by the sensor 702 (with or without pre-processing) may be provided as inputs to a trained statistical model (e.g., a statistical model trained using data gathered by sensors 602, 604, and 606) and the responsive output generated by the trained statistical model may be used to determine spatial information for one or more of the segments of the multi-segment articulated rigid body system. For example, the responsive output may indicate (or may be processed to determine) position and/or orientation for each of one or more segments of an articulated rigid body system. As one non-limiting example, movement sensor may be coupled to a user's wrist and the responsive output may indicate (or may be processed to determine) the position and/or orientation of the user's hand, forearm, and/or upper arm in 3D space (e.g., in a torso reference frame or any other suitable reference frame). As another example, the responsive output may indicate (or may be processed to determine) joint angles between two or more connected segments of the multi-segment articulated rigid body system. As one non-limiting example, movement sensor may be coupled to a user's wrist and the responsive output may indicate (or may be processed to determine) the joint angle between the user's hand and forearm and/or between the user's forearm and upper arm.

Although there only a single motion sensor shown in the illustrative example of FIG. 7, in another example, there may be two movement sensors coupled to two of the three segments. Measurements obtained by two sensors (with or without pre-processing) may be provided as inputs to a trained statistical model (e.g., a statistical model trained using data gathered by sensors 602, 604, and 606) and the responsive output generated by the trained statistical model may be used to determine spatial information for one or more of the segments of the multi-segment articulated rigid body system. For example, the responsive output may indicate (or may be processed to determine) position for each of one or more segments of an articulated rigid body system (e.g., relative to an anchor point of the anchored segment or with respect to any other suitable reference frame).

More generally, in some embodiments, an articulated rigid body system may have multiple segments and measurements obtained from autonomous movement sensors coupled to a proper subset of the segments (such that there are fewer autonomous movement sensors than there are segments) may be used to estimate spatial information for any segment(s) to which an autonomous movement sensor is not coupled to (e.g., to estimate position and/or orientation information for any segment(s) to which an autonomous movement sensor is not coupled to, estimate position information for any segment(s) to which an autonomous movement sensor is coupled to, etc.).

Figure 8:
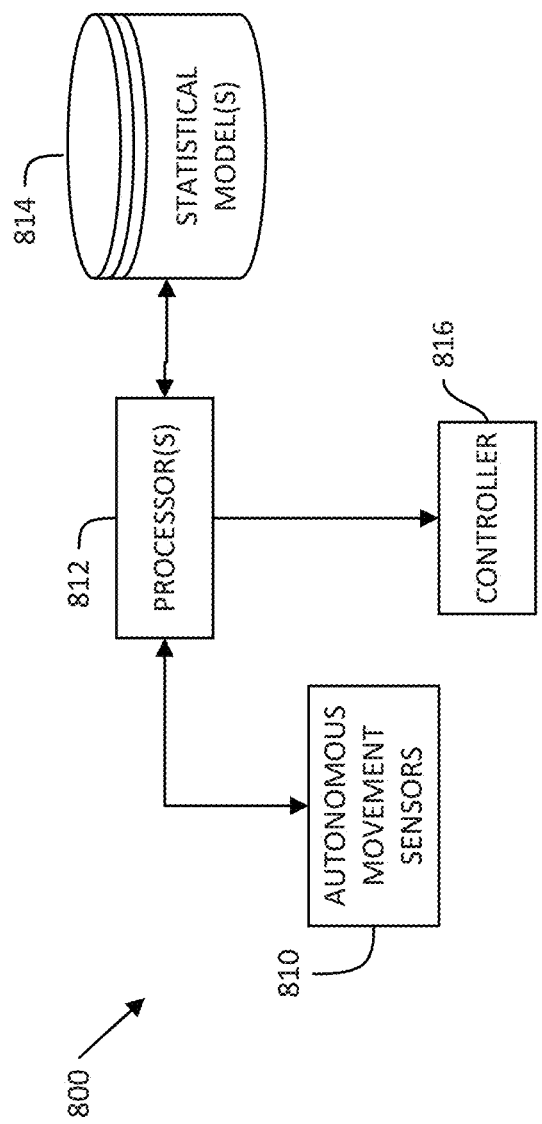
FIG. 8 is a schematic diagram of a computer-based system for generating spatial information in accordance with some embodiments of the technology described herein.

FIG. 8 is a schematic diagram of a system 800 for generating spatial information in accordance with some embodiments of the technology described herein. The system includes a plurality of autonomous movement sensors 810 configured to record signals resulting from the movement of portions of a human body. As used herein, the term "autonomous movement sensors" refers to sensors configured to measure the movement of body segments without requiring the use of external sensors, examples of which include, but are not limited to, cameras or global positioning systems. Autonomous movement sensors 810 may include one or more Inertial Measurement Units (IMUs), which measure a combination of physical aspects of motion, using, for example, an accelerometer and a gyroscope. In some embodiments, IMUs may be used to sense information about the movement of the part of the body on which the IMU is attached and information derived from the sensed data (e.g., position and/or orientation information) may be tracked as the user moves over time. For example, one or more IMUs may be used to track movements of portions of a user's body proximal to the user's torso (e.g., arms, legs) as the user moves over time.

In some embodiments, autonomous movement sensors may be arranged on one or more wearable devices configured to be worn around the lower arm or wrist of a user. In such an arrangement, the autonomous movement sensor may be configured to track movement information (e.g., positioning and/or orientation over time) associated with one or more arm segments, to determine, for example whether the user has raised or lowered his or her arm.

Each of autonomous movement sensors 810 may include one or more movement sensing components configured to sense movement information. In the case of IMUs, the movement sensing components may include one or more accelerometers, gyroscopes, magnetometers, or any combination thereof to measure characteristics of body motion, examples of which include, but are not limited to, acceleration, angular velocity, and sensed magnetic field around the body.

In some embodiments, the output of one or more of the movement sensing components may be processed using hardware signal processing circuitry (e.g., to perform amplification, filtering, and/or rectification). In other embodiments, at least some signal processing of the output of the movement sensing components may be performed in software. Thus, signal processing of autonomous signals recorded by autonomous movement sensors 810 may be performed in hardware, software, or by any suitable combination of hardware and software, as aspects of the technology described herein are not limited in this respect.

In some embodiments, the recorded sensor data may be processed to compute additional derived measurements that are then provided as input to a statistical model. For example, recorded signals from an IMU sensor may be processed to derive an orientation signal that specifies the orientation of a rigid body segment over time. Autonomous movement sensors 810 may implement signal processing using components integrated with the movement sensing components, or at least a portion of the signal processing may be performed by one or more components in communication with, but not bodily integrated with the movement sensing components of the autonomous sensors.

In some embodiments, at least some of the plurality of autonomous sensors 810 are arranged as a portion of a wearable device configured to be worn on or around part of a user's body. For example, in one non-limiting example, one or more IMU sensors may be arranged on an adjustable and/or elastic band such as a wristband or armband configured to be worn around a user's wrist or arm. Alternatively, at least some of the autonomous sensors may be arranged on a wearable patch configured to be affixed to a portion of the user's body.

System 800 also includes one or more computer processors 812 programmed to communicate with autonomous movement sensors 810. For example, signals recorded by one or more of the autonomous sensors 810 may be provided to processor(s) 812, which may be programmed to perform signal processing, non-limiting examples of which are described above. Processor(s) 812 may be implemented in hardware, firmware, software, or any combination thereof. Additionally, processor(s) 812 may be co-located on a same wearable device as one or more of the autonomous sensors or may be at least partially located remotely (e.g., processing may occur on one or more network-connected processors).

System 800 also includes datastore 814 in communication with processor(s) 812. Datastore 814 may include one or more storage devices configured to store information describing a statistical model used for generating spatial information for one or more segments of a multi-segment articulated rigid body system based on signals recorded by autonomous sensors 810 in accordance with some embodiments. Processor(s) 812 may be configured to execute one or more algorithms that process signals output by the autonomous movement sensors 810 to train a statistical model stored in datastore 814, and the trained (or retrained) statistical model may be stored in datastore 814 for later use in generating spatial information. Non-limiting examples of statistical models that may be used in accordance with some embodiments to generate spatial information for articulated rigid body system segments based on recorded signals from autonomous sensors are discussed herein.

In some embodiments, processor(s) 812 may be configured to communicate with one or more of autonomous movement sensors 810, for example to calibrate the sensors prior to measurement of movement information. For example, a wearable device may be positioned in different orientations on or around a part of a user's body and calibration may be performed to determine the orientation of the wearable device and/or to perform any other suitable calibration tasks. Calibration of autonomous movement sensors 810 may be performed in any suitable way, and embodiments are not limited in this respect. For example, in some embodiments, a user may be instructed to perform a particular sequence of movements and the recorded movement information may be matched to a template by virtually rotating and/or scaling the signals detected by the sensors. In some embodiments, calibration may involve changing the offset(s) of one or more accelerometers, gyroscopes, or magnetometers.

System 800 also includes one or more controllers 816 configured to receive a control signal based, at least in part, on processing by processor(s) 812. As discussed in more detail below, processor(s) 812 may implement one or more trained statistical models 814 configured to predict spatial information based, at least in part, on signals recorded by one or more autonomous sensors 810 worn by a user. One or more control signals determined based on the output of the trained statistical model(s) may be sent to controller 816 to control one or more operations of a device associated with the controller. In some embodiments, controller 816 comprises a display controller configured to instruct a visual display to display a graphical representation of a computer-based musculo-skeletal representation (e.g., a graphical representation of the user's body or a graphical representation of a character (e.g., an avatar in a virtual reality environment)) based on the predicted spatial information. For example, a computer application configured to simulate a virtual reality environment may be instructed to display a graphical representation of the user's body orientation, positioning and/or movement within the virtual reality environment based on the output of the trained statistical model(s). The positioning and orientation of different parts of the displayed graphical representation may be continuously updated as signals are recorded by the autonomous movement sensors 810 and processed by processor(s) 812 using the trained statistical model(s) 814 to provide a computer-generated representation of the user's movement that is dynamically updated in real-time. In other embodiments, controller 816 comprises a controller of a physical device, such as a robot. Control signals sent to the controller may be interpreted by the controller to operate one or more components of the robot to move in a manner that corresponds to the movements of the user as sensed using the autonomous movement sensors 810.

Controller 816 may be configured to control one or more physical or virtual devices, and embodiments of the technology described herein are not limited in this respect. Non-limiting examples of physical devices that may be controlled via controller 816 include consumer electronics devices (e.g., television, smartphone, computer, laptop, telephone, video camera, photo camera, video game system, appliance, etc.), vehicles (e.g., car, marine vessel, manned aircraft, unmanned aircraft, farm machinery, etc.), robots, weapons, or any other device that may receive control signals via controller 816.

In yet further embodiments, system 800 may not include one or more controllers configured to control a device. In such embodiments, data output as a result of processing by processor(s) 812 (e.g., using trained statistical model(s) 814) may be stored for future use (e.g., for analysis of a health condition of a user or performance analysis of an activity the user is performing).

In some embodiments, during real-time movement tracking, information sensed from a single armband/wristband wearable device that includes at least one IMU is used to reconstruct body movements, such as reconstructing the position and orientation of both the forearm and upper arm relative to a torso reference frame using the single arm/wrist-worn device, and without the use of external devices or position determining systems. For brevity, determining both position and orientation may also be referred to herein generally as determining movement.

Some embodiments are directed to using a statistical model for predicting spatial information for segments of an articulated rigid body system representing body parts of a user based on signals recorded from wearable autonomous sensors. The statistical model may be used to predict the spatial information without having to place sensors on each segment of the rigid body that is to be represented in a computer-generated musculo-skeletal representation of user's body. As discussed briefly above, the types of joints between segments in a multi-segment articulated rigid body model constrain movement of the rigid body. Additionally, different individuals tend to move in characteristic ways when performing a task that can be captured in statistical patterns of individual user behavior. At least some of these constraints on human body movement may be explicitly incorporated into statistical models used for prediction in accordance with some embodiments. Additionally or alternatively, the constraints may be learned by the statistical model though training based on recorded sensor data. As described in more detail below, the constraints may comprise part of the statistical model itself being represented by information (e.g., connection weights between nodes) in the model.

In some embodiments, system 800 may be trained to predict spatial information as a user moves. In some embodiments, the system 800 may be trained by recording signals from autonomous movement sensors 810 (e.g., IMU sensors) and position information recorded from position sensors worn by one or more users as the user(s) perform one or more movements. The position sensors may measure the position of each of a plurality of spatial locations on the user's body as the one or more movements are performed during training to determine the actual position of the body segments. After such training, the system 800 may be configured to predict, based on a particular user's autonomous sensor signals, spatial information (e.g., a set of joint angles) that enable the generation of spatial information and using the spatial information to generate a musculo-skeletal representation without the use of the position sensors.

In some embodiments, after system 800 is trained to predict, based on a particular user's autonomous sensor signals, the spatial information, a user may utilize the system 800 to perform a virtual or physical action without using position sensors. For example, when the system 800 is trained to predict with high accuracy (e.g., at least a threshold accuracy), the spatial information, the predictions themselves may be used to determine the musculo-skeletal position information used to generate a musculo-skeletal representation of the user's body.

As discussed above, some embodiments are directed to using a statistical model for generation of spatial information to enable the generation of a computer-based musculo-skeletal representation. In some embodiments, the statistical model may be used to predict the spatial musculo-skeletal position information based on signals gathered by a single IMU sensor worn by the user (e.g., on his wrist) as the user performs one or more movements.

Figure 9A:
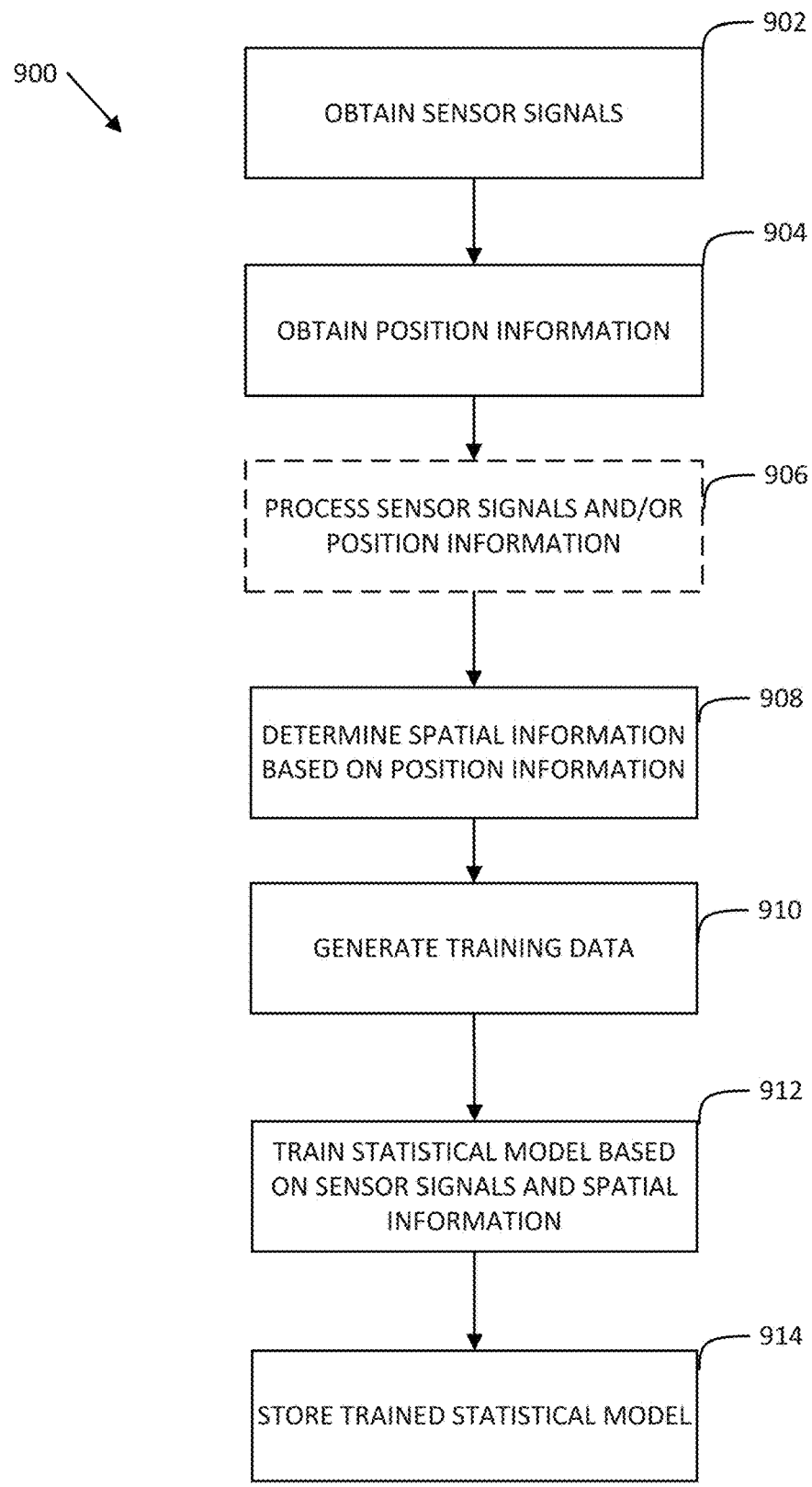
FIG. 9A is a flowchart of an illustrative process for training a statistical model for generating spatial information, in accordance with some embodiments of the technology described herein.

FIG. 9A describes a process 900 for generating (sometimes termed "training" herein) a statistical model using signals recorded from autonomous sensors worn by one or more users. Process 900 may be executed by any suitable computing device(s), as aspects of the technology described herein are not limited in this respect. For example, process 900 may be executed by processors 812 described with reference to FIG. 8. As another example, one or more acts of process 900 may be executed using one or more servers (e.g., servers included as a part of a cloud computing environment). For example, at least a portion of act 912 relating to training of a statistical model (e.g., a neural network) may be performed using a cloud computing environment.

Process 900 begins at act 902, where a plurality of sensor signals are obtained for one or multiple users performing one or more movements (e.g., typing on a keyboard, moving a video game controller, moving a virtual reality controller). In some embodiments, the plurality of sensor signals may be recorded as part of process 900. In other embodiments, the plurality of sensor signals may have been recorded prior to the performance of process 900 and are accessed (rather than recorded) at act 902.

In some embodiments, the plurality of sensor signals may include sensor signals recorded for a single user performing a single movement or multiple movements. The user may be instructed to perform a sequence of movements for a particular task (e.g., opening a door) and sensor signals corresponding to the user's movements may be recorded as the user performs the task he/she was instructed to perform. The sensor signals may be recorded by any suitable number of autonomous movement sensors located in any suitable location(s) to detect the user's movements that are relevant to the task performed. For example, after a user is instructed to perform a task with his/her right hand, the sensor signals may be recorded by one or more IMU sensors arranged to predict the joint angle of the user's arm relative to the user's torso. As another example, after a user is instructed to perform a task with his/her leg (e.g., to kick an object), sensor signals may be recorded by one or more IMU sensors arranged to predict the joint angle of the user's leg relative to the user's torso.

In some embodiments, the sensor signals obtained in act 902 correspond to signals obtained from one or multiple IMU sensors and a statistical model may be trained based on the sensor signals recorded using the IMU sensor(s). The trained statistical model may be trained, using the recorded sensor signal, to predict spatial information for one or more of the user's limbs which may be moving as the user performs a task (e.g., position and/or orientation of the user's hand, forearm, upper arm, and/or wrist, and/or one or more joint angles between the hand, forearm and/or upper arm). For example, the statistical model may be trained to predict spatial information for the wrist and/or hand during performance of a task such as grasping and twisting an object such as a doorknob.

In some embodiments, the sensor signals obtained at act 902 may be obtained from multiple IMU sensors, but the statistical model being trained may be configured to receive input from a subset of the multiple IMU sensors (e.g., only a single IMU sensor, which for example may be worn on a user's wrist). In such embodiments, during training, sensor signals obtained from a subset of the multiple IMUs may be provided (with or without pre-processing) as input to the statistical model being trained while sensor signals obtained from the other of the multiple IMUs (i.e., the IMUs not in the subset) may be used (with or without pre-processing) to generate data representing the target (or "ground truth") output that the statistical model is to produce in response to the input signals. As further described below, in some embodiments, the sensor signals obtained by the other of the multiple IMUs may be combined together with position data obtained by one or more autonomous or non-autonomous position or movement sensors to generate data representing the target output. In this way, data from a first set of one or more autonomous movement sensors and one or more other sensors (e.g., one or more non-autonomous position sensors alone or in combination with one or more autonomous movement sensors not in the first set) may be used to train a statistical model, in some embodiments.

In some embodiments, the sensor signals obtained in act 902 are recorded at multiple time points as a user performs one or multiple movements. As a result, the recorded signal for each sensor may include data obtained at each of multiple time points. Assuming that n autonomous sensors are arranged to simultaneously measure the user's movement information during performance of a task, the recorded sensor signals for the user may comprise a time series of K m-dimensional vectors $\{x_k | 1 \leq k \leq K\}$ at time points $t_1, t_2, \ldots, t_K$ during performance of the movements. In some embodiments, n may be different from m.

In some embodiments, a user may be instructed to perform a task multiple times and the sensor signals and position information may be recorded for each of multiple repetitions of the task by the user. In some embodiments, the plurality of sensor signals may include signals recorded for multiple users, each of the multiple users performing the same task one or more times. Each of the multiple users may be instructed to perform the task and sensor signals and position information corresponding to that user's movements may be recorded as the user performs (once or repeatedly) the task he/she was instructed to perform. Collecting sensor signals and position information from a single user performing the same task repeatedly and/or from multiple users performing the same task one or multiple times facilitates the collection of sufficient training data to generate a statistical model that can accurately predict spatial information for segments of an articulated rigid body model of a user during performance of the task by the user.

In some embodiments, a user-independent statistical model may be generated based on training data corresponding to the recorded signals from multiple users, and as the system is used by a user, the statistical model is trained based on recorded sensor data such that the statistical model learns the user-dependent characteristics to refine the prediction capabilities of the system for the particular user, for example when using a variational autoencoder with a generative model.

In some embodiments, the plurality of sensor signals may include signals recorded for a user (or each of multiple users) performing each of multiple tasks one or multiple times. For example, a user may be instructed to perform each of multiple tasks (e.g., grasping an object, pushing an object, and pulling open a door) and signals corresponding to the user's movements may be recorded as the user performs each of the multiple tasks he/she was instructed to perform. Collecting such data may facilitate developing a statistical model for predicting spatial information associated with multiple different actions that may be taken by the user. For example, training data that incorporates spatial information for multiple actions may facilitate generating a statistical model for predicting spatial information.

As discussed above, the sensor data obtained at act 902 may be obtained by recording sensor signals as each of one or multiple users performs each of one or more tasks one or more multiple times. As the user(s) perform the task(s), position information describing the spatial position of different body segments during performance of the task(s) may be obtained in act 904. In some embodiments, the position information is obtained using one or more external devices or systems that track the position of different points on the body during performance of a task. For example, a motion capture system, a laser scanner, a device to measure mutual magnetic induction, or some other system configured to capture position information may be used. As one non-limiting example, a plurality of position sensors may be placed on segments of the fingers of the right hand and a motion capture system may be used to determine the spatial location of each of the position sensors as the user performs a task such as grasping an object. The sensor data obtained at act 902 may be recorded simultaneously with recording of the position information obtained in act 904. In this example, position information indicating the position of each finger segment over time as the grasping motion is performed is obtained.

Next, process 900 proceeds to act 906, where the autonomous sensor signals obtained in act 902 and/or the position information obtained in act 904 are optionally processed. For example, the autonomous sensor signals and/or the position information signals may be processed using amplification, filtering, rectification, and/or other types of signal processing techniques. As another example, the autonomous sensor signals and/or the position information signals may be transformed using one or more spatial (e.g., coordinate) transformations, angle transformations, time derivatives, etc.

In embodiments where multiple sensors are used to obtain data ((e.g., multiple IMU sensors, at least one IMU sensor and at least one non-autonomous position sensor, etc.) configured to simultaneously record information during performance of a task, the sensor data for the sensors may be recorded using the same or different sampling rates. When the sensor data is recorded at different sampling rates, at least some of the sensor data may be resampled (e.g., up-sampled or down-sampled) such that all sensor data provided as input to the statistical model corresponds to time series data at the same time resolution. Resampling at least some of the sensor data may be performed in any suitable way including, but not limited to using interpolation for upsampling and using decimation for downsampling.

In addition to or as an alternative to resampling at least some of the sensor data when recorded at different sampling rates, some embodiments employ a statistical model configured to accept multiple inputs asynchronously. For example, the statistical model may be configured to model the distribution of the "missing" values in the input data having a lower sampling rate. Alternatively, the timing of training of the statistical model occur asynchronously as input from multiple sensor data measurements becomes available as training data.

Next, process 900 proceeds to act 908, where spatial information is determined based on the position information (as collected in act 904 or as processed in act 906) and/or at least some of the sensed signals obtained at act 902. In some embodiments, rather than using recorded spatial (e.g., x, y, z) coordinates corresponding to the position sensors as training data to train the statistical model, a set of derived spatial values are determined based on the recorded position information, and the derived values are used as training data for training the statistical model.

For example, using information about the constraints between connected pairs of rigid segments in the articulated rigid body model, the position information may be used to determine joint angles that define angles between each connected pair of rigid segments at each of multiple time points during performance of a task. Accordingly, the position information obtained in act 904 may be represented by a vector of n joint angles at each of a plurality of time points, where n is the number of joints or connections between segments in the articulated rigid body model.

Next, process 900 proceeds to act 910, where the time series information obtained at acts 902 and 908 is combined to create training data used for training a statistical model at act 910. The obtained data may be combined in any suitable way. In some embodiments, each of the autonomous sensor signals obtained at act 902 may be associated with a task or movement within a task corresponding to the spatial information (e.g., positions, orientations, and/or joint angles) determined based on the sensed signals obtained at act 902 and/or positional information recorded in act 904 as the user performed the task or movement. In this way, at least some of the sensor signals obtained at act 902 may be associated with corresponding spatial information (e.g., positions, orientations, and joint angles) and the statistical model may be trained to predict such spatial information when particular sensor signals are recorded during performance of a particular task, as described below with reference to FIG. 9B.

Next, process 900 proceeds to act 912, where a statistical model for generating spatial information for one or more segments of an articulated rigid body system is trained using the training data generated at act 910. The statistical model being trained may take as input a sequence of data sets each of the data sets in the sequence comprising an n-dimensional vector of autonomous sensor data. The statistical model may provide output that indicates, for each of one or more tasks or movements that may be performed by a user, information that indicates (directly or indirectly) spatial information (e.g., position of, orientation of, joint angles between) for one or more segments of a multi-segment articulated rigid body model of the human body. As one non-limiting example, the statistical model may be trained to predict a set of joint angles for segments in the fingers in the hand over time as a user grasps an object. In this example, the trained statistical model may output, a set of predicted joint angles for joints in the hand corresponding to the sensor input.

In some embodiments, the statistical model may be a neural network and, for example, may be a recurrent neural network. In some embodiments, the recurrent neural network may be a long short-term memory (LSTM) neural network. It should be appreciated, however, that the recurrent neural network is not limited to being an LSTM neural network and may have any other suitable architecture. For example, in some embodiments, the recurrent neural network may be a fully recurrent neural network, a recursive neural network, a variational autoencoder, a Hopfield neural network, an associative memory neural network, an Elman neural network, a Jordan neural network, an echo state neural network, a second order recurrent neural network, and/or any other suitable type of recurrent neural network. In other embodiments, neural networks that are not recurrent neural networks may be used. For example, deep neural networks, convolutional neural networks, and/or feedforward neural networks, may be used.

In some of the embodiments in which the statistical model is a neural network, the output layer of the neural network may provide a set of output values corresponding to a respective set of possible musculo-skeletal position characteristics (e.g., positions of one or more segments, orientation of one or more segments, joint angles between any connected segments). In this way, the neural network may operate as a non-linear regression model configured to predict musculo-skeletal position characteristics from raw or pre-processed sensor measurements. It should be appreciated that, in some embodiments, any other suitable non-linear regression model may be used instead of a neural network, as aspects of the technology described herein are not limited in this respect.

It should be appreciated that aspects of the technology described herein are not limited to using neural networks, as other types of statistical models may be employed in some embodiments. For example, in some embodiments, the statistical model may comprise a hidden Markov model, a Markov switching model with the switching allowing for toggling among different dynamic systems, dynamic Bayesian networks, and/or any other suitable graphical model having a temporal component. Any such statistical model may be trained at act 912 using the sensor data obtained at act 902.

In some embodiments, a generative statistical model (e.g., a graphical model) may be employed and spatial information may be obtained from the generative statistical model by application of one or more online inference algorithms. In some embodiments, the generative statistical model may not require a priori training. Non-limiting examples of online inference algorithms include Kalman filtering, extended Kalman filtering, unscented Kalman filtering, and particle filtering.

As another example, in some embodiments, the statistical model may take as input, features derived from the sensor data obtained at act 902. In such embodiments, the statistical model may be trained at act 912 using features extracted from the sensor data obtained at act 902. Input features to be provided as training data to the statistical model may be derived from the sensor data obtained at act 902 in any suitable way. For example, the sensor data may be analyzed as time series data using wavelet analysis techniques (e.g., continuous wavelet transform, discrete-time wavelet transform, etc.), Fourier-analytic techniques (e.g., short-time Fourier transform, Fourier transform, etc.), and/or any other suitable type of time-frequency analysis technique. As one non-limiting example, the sensor data may be transformed using a wavelet transform and the resulting wavelet coefficients may be provided as inputs to the statistical model, which may be a neural network or any other suitable type of non-linear regression model, in some embodiments. As another non-limiting example, the sensor data may be transformed using one or more spatial transformations (e.g., coordinate transformations), conversions between angles and quaternia, time derivatives, relative angles, etc.

In some embodiments, at act 912, values for parameters of the statistical model may be estimated from the training data generated at act 910. For example, when the statistical model is a neural network, parameters of the neural network (e.g., weights) may be estimated from the training data. In some embodiments, parameters of the statistical model may be estimated using gradient descent, stochastic gradient descent, and/or any other suitable iterative optimization technique. In some embodiments where the statistical model is a recurrent neural network (e.g., an LSTM), the statistical model may be trained using stochastic gradient descent and backpropagation through time. The training may employ a mean squared error loss function and/or any other suitable loss function, as aspects of the technology described herein are not limited in this respect.

Next, process 900 proceeds to act 914, where the trained statistical model is stored (e.g., in datastore 814). The trained statistical model may be stored using any suitable format, as aspects of the technology described herein are not limited in this respect. In this way, the statistical model generated during execution of process 900 may be used at a later time, for example, in accordance with the process described below with reference to FIG. 9B.

Figure 9B:
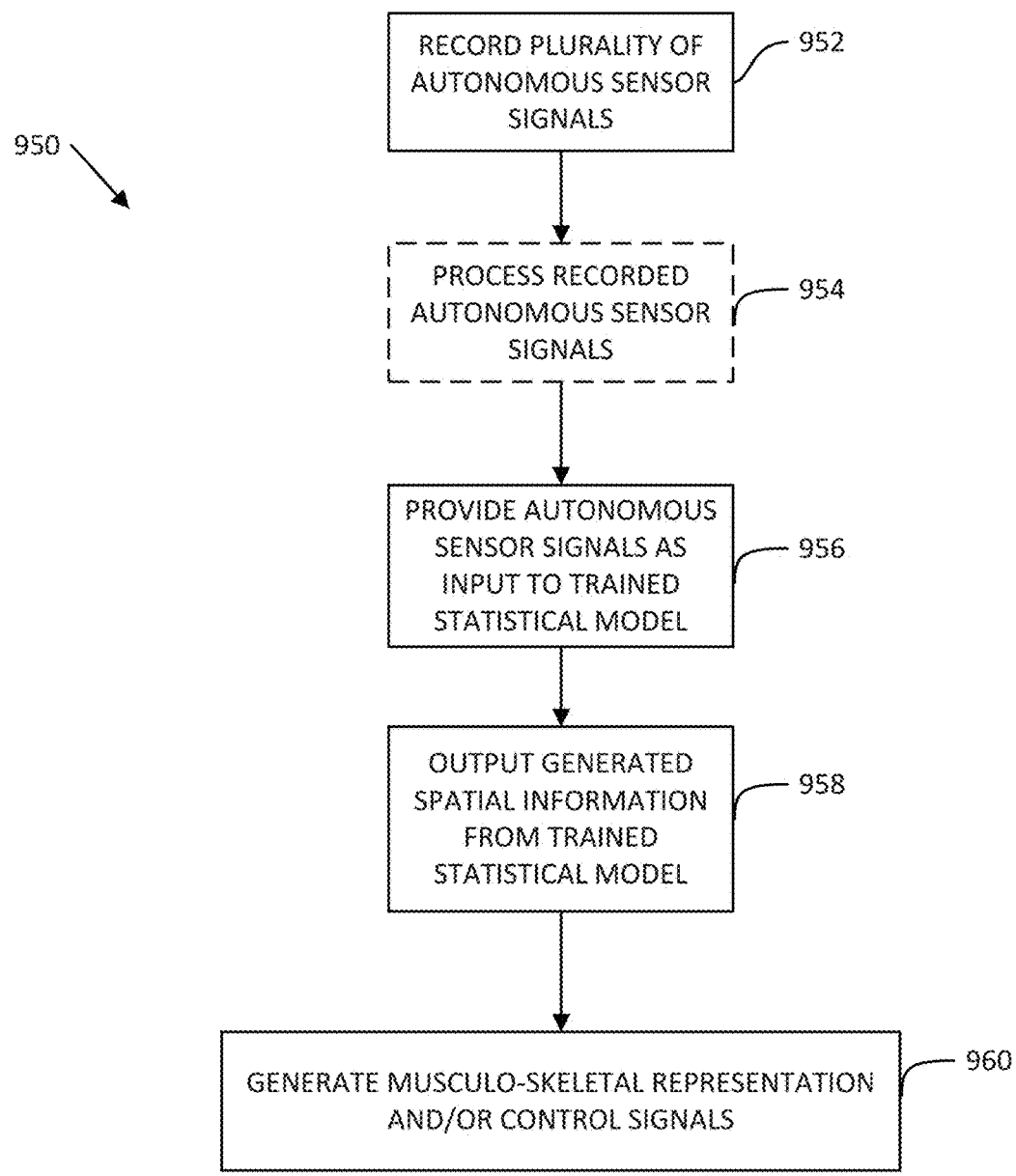
FIG. 9B is a flowchart of an illustrative process for generating spatial information by providing movement sensor measurements to a trained statistical model, in accordance with some embodiments of the technology described herein.

FIG. 9B is a flowchart of an illustrative process 950 for generating spatial information by using recorded movement sensor measurements from at least one (and, in some embodiments, a single) autonomous sensor and a trained statistical model, in accordance with some embodiments of the technology described herein.

Process 950 begins in act 952, where signals are obtained from one or more of autonomous movement sensors arranged on or near the surface of a user's body to record activity associated with movements of the body during performance of a task. In some embodiments, the autonomous movement sensor(s) consist of a single IMU sensor. In other embodiments, the autonomous movement sensors consist of multiple IMU sensors. In some embodiments, the autonomous movement sensor(s) comprise one or more accelerometers, one or more gyroscopes, and/or one or more magnetometers. The autonomous movement sensor(s) may be arranged on a wearable device configured to be worn on or around a part of the user's body, such as the user's arm or leg.

Process 950 then proceeds to act 954, where the signals recorded by the autonomous sensors are optionally processed. For example, the signals may be processed using amplification, filtering, rectification, and/or other types of signal processing techniques. As another example, the signals may be processed using one or more spatial transformations (e.g., coordinate transformations), conversions between angles and quaternia, and/or time derivatives.

In some embodiments, filtering includes temporal filtering implemented using convolution operations and/or equivalent operations in the frequency domain (e.g., after the application of a discrete Fourier transform). In some embodiments, the signals are processed in the same or similar manner as the signals recorded in act 902 of process 900 described above and used as training data to train the statistical model.

Process 950 then proceeds to act 956, where the autonomous sensor signals are provided as input to a statistical model (e.g., a neural network) trained using one or more of the techniques described above in connection with process 900. In some embodiments that continuously record autonomous signals, the continuously recorded autonomous signals (raw or processed) may be continuously or periodically provided as input to the trained statistical model for prediction of spatial information (e.g., positions of one or more segments, orientation of one or more segments, joint angles between any connected segments) for the given set of input sensor data. As discussed above, in some embodiments, the trained statistical model is a user-independent model trained based on autonomous sensor and position information measurements from a plurality of users. In other embodiments, the trained model is a user-dependent model trained on data recorded from the individual user from which the data recorded in act 952 is also acquired.

After the trained statistical model receives the sensor data as a set of input parameters, process 900 proceeds to act 958, where generated spatial information is output from the trained statistical model. As discussed above, in some embodiments, the generated spatial information may comprise position, orientation, and/or angular information (e.g., a set of joint angles) for segments of a multi-segment articulated rigid body model representing at least a portion of the user's body.

After spatial information is generated at act 958, process 950 proceeds to act 960, where the spatial information may be used in any of numerous ways. For example, in some embodiments, the spatial information may be used to generate a computer-based musculo-skeletal representation based on the spatial information generated at act 958. The computer-based musculo-skeletal representation may be generated in any suitable way. For example, a computer-based musculo-skeletal model of the human body may include multiple rigid body segments, each of which corresponds to one or more skeletal structures in the body. For example, the upper arm may be represented by a first rigid body segment, the lower arm may be represented by a second rigid body segment the palm of the hand may be represented by a third rigid body segment, and each of the fingers on the hand may be represented by at least one rigid body segment (e.g., at least fourth-eighth rigid body segments). A set of joint angles between connected rigid body segments in the musculo-skeletal model may define the orientation of each of the connected rigid body segments relative to each other and a reference frame, such as the torso of the body. As new sensor data is measured and processed by the statistical model to provide new predictions of the spatial information (e.g., an updated set of joint angles), the computer-based musculo-skeletal representation of the user's body may be updated based on the updated set of joint angles determined based on the output of the statistical model. In this way the computer-based musculo-skeletal representation is dynamically updated in real-time as autonomous sensor data is continuously recorded.

The computer-based musculo-skeletal representation may be represented and stored in any suitable way, as embodiments of the technology described herein are not limited with regard to the particular manner in which the representation is stored. Additionally, although referred to herein as a "musculo-skeletal" representation, to reflect that muscle activity may be associated with the representation in some embodiments, as discussed in more detail below, it should be appreciated that some musculo-skeletal representations used in accordance with some embodiments may correspond to skeletal structures only, muscular structures only or a combination of skeletal structures and muscular structures in the body.

As another example, in some embodiments, the spatial information may be used to generate one or more control signals which may be sent to a controller as part of act 960 of process 950. For example, when the controller is a display controller, the control signal(s) may instruct a display in communication with the display controller to display a graphical rendering based on the generated spatial representation. For a computer application that provides a virtual reality environment, the graphical rendering may be a rendering of the user's body or another computer-generated character (e.g., an avatar) based on a current state of the musculo-skeletal representation. As sensor data is collected, the rendered character may be dynamically updated to provide an animation of the rendered character that mimics the movements of the user wearing the wearable device including the autonomous sensors. In a virtual reality environment, a result of the character's animation may be the ability of the animated character to interact with objects in the virtual reality environment, examples of which include, but are not limited to, grasping a virtual object.

In some embodiments, in which the controller is configured to control a physical device (e.g., a robot), the control signal(s) sent to the controller may instruct the physical device to perform one or more actions corresponding to the generated spatial information. For example, when the device being controlled is a robot, the control signal(s) may instruct the controller of the robot to mimic the movements of the user or otherwise control an operation of the robot based on the generated spatial information.

In yet further embodiments, the generated spatial information may be used to track the user's movements over time and provide a control signal to a controller that provides feedback to the user about the tracked movements. For example, the generated and dynamically updated spatial information may track the position of the user's hands as the user is typing on a keyboard and provide feedback to the user when it is determined that the user is likely to experience muscle fatigue due to the position of their hands as they type. The feedback may be provided in any suitable way using, for example, haptic feedback, audio feedback, and/or visual feedback as embodiments of the technology described herein are not limited based on how the feedback is provided.

In some embodiments at least some of the sensor data recorded during use of the system may be used as training data to train the statistical model to enable the model to continue to refine the statistical relationships between movement-based information recorded by the autonomous sensors and spatial information output by the statistical model. Continuous training of the statistical model may result in improved performance of the model in generating spatial information for movements that are performed by the user in a consistent manner.

Although process 950 is described herein as being performed after process 900 has completed and a statistical model has been trained, in some embodiments, process 900 and 950 may be performed together. For example, the statistical model may be trained in real-time, as a user is performing movements to interact with a virtual or physical object, and the trained statistical model may be used as soon as the model has been trained sufficiently to provide reliable predictions. In some embodiments, this may be performed using a variational autoencoder.

In some embodiments, during the learning phase the measurement data generated from movement sensors affixed to the non-anchored segment may be augmented with additional measurement data. This additional measurement data may be data generated from any secondary measurement system and, which may be used to precisely establish the position and orientation of the non-anchored segment. In some embodiments, the secondary measurement system may be an external system, such as GPS, LIDAR, or the like. In some embodiments, the additional measurement data may be generated from an IMU coupled to the anchored segment together with measurements or estimates of segment lengths. It should be appreciated, however, that such additional measurement data is not required and may be used, when available, to augment already available measurement data.

In some embodiments, in the scenario involving a user's arm movement, the statistical model can take on different forms. For example, in some embodiments, the statistical model may be trained to determine the position of the sensor on the wrist from orientation information of the forearm, which may be obtained from a single IMU (e.g., using sensor fusion techniques); from this information, inverse kinematics may be used to determine aspects of the orientation of the upper arm. As another example, the statistical model may be trained to determine the orientation of the upper arm; from this information, forward kinematics may be used to determine the position of the wrist. Converting between the two viewpoints (wrist position to upper arm orientation, or vice versa) may requires additional information, such as information specifying arm segment lengths. Such information may be provided separately or, in some embodiments, may be inferred from the measurement data.

In some embodiments, a movement device may be an inertial measurement unit (IMU). The IMU may be of any suitable type, as aspects of the technology described herein are not limited in this respect. In some embodiments, an IMU may comprise one or more accelerometers, one or more gyroscopes, one or magnetometers, and/or any other suitable device for measuring movement. In some embodiments, the IMU may be a nine-axis device. In some embodiments, the IMU may be a commercially-available IMU sensor, or it may be some other wearable technology (e.g., an Apple® watch, the FitBit™ activity tracker, and many others) that provides (or is augmented to provide) the relevant IMU-type data.

As described herein, in some embodiments, a trained statistical model may be used to generate spatial information data. In some embodiments, where the trained statistical model is a neural network, the neural network may be trained at least in part by using commercially-available or open source software libraries, such as the Theano Python library.

The techniques described herein provide significant advantages. As has been described, in some embodiments, a movement sensor (e.g., an IMU) may be positioned on a user's wrist and may be configured to generate a stream of measurements. In turn, the generated measurements may be used together with the statistical models described herein to estimate the position and/or orientation of the user's wrist in 3D space. In some embodiments, the estimated position may be relative to a fixed point such as the user's shoulder.

Thus, it should be appreciated that the approach herein discloses a system that reconstructs the configuration dynamics of a mechanical system consisting of articulated rigid body segments without measuring the absolute position and without affixing a sensor to each segment of the rigid body system. In some embodiments, the mechanical system may be a human skeleton, though the techniques described herein may be used with any rigid body mechanical system wherein it is desired to measure the absolute position of a set of segments that comprise the articulated rigid body system without necessarily using a sensor on each segment during the real-time analysis phase. Thus, in some embodiments, training data may be collected by placing one or more devices with autonomous sensors on a subset of the rigid body system. Such sensors may include one or more IMUs, one or more accelerometers, one or more gyroscopes, and/or one or more magnetometers.

In some embodiments, measurement data collected using movement sensors may be used in conjunction with a trained statistical model to obtain spatial information for segments of an articulated rigid body system (e.g., position of one or more segments, orientation of one or more segments, angles between one or more pairs of segments, etc.). The statistical model may be used to obtain spatial information for segments that do not have any attached sensors. In some embodiments, the subject matter herein can use algorithms that use explicit articulation constraints and patterns of rigid body system movements, such as model-based approaches, constraints, and statistical priors. In some embodiments, the techniques can use statistical models that encode articulation constraints and patterns of rigid body system movements learned from data. Non-limiting examples of such statistical models include recurrent neural networks, long short-term memory neural networks, and/or any other suitable type of neural networks. Non-limiting examples of applications of the disclosed subject matter include uses for reconstructing human movements with wearable devices, such as reconstructing the movement of both the forearm and upper arm using a single wrist-worn device.

It should be appreciated that, although the techniques described herein may be applied for controlling virtual reality applications, the techniques described herein are not limited to only such applications. For example, the techniques described herein may be used for controlling a robot.

The techniques herein generally provide for the above-described improvements to a technology or technical field (namely, motion sensing devices, systems and methods), as well as the specific technological improvements to other kinematics-based interfaces and process, such as described above.

Figure 10:
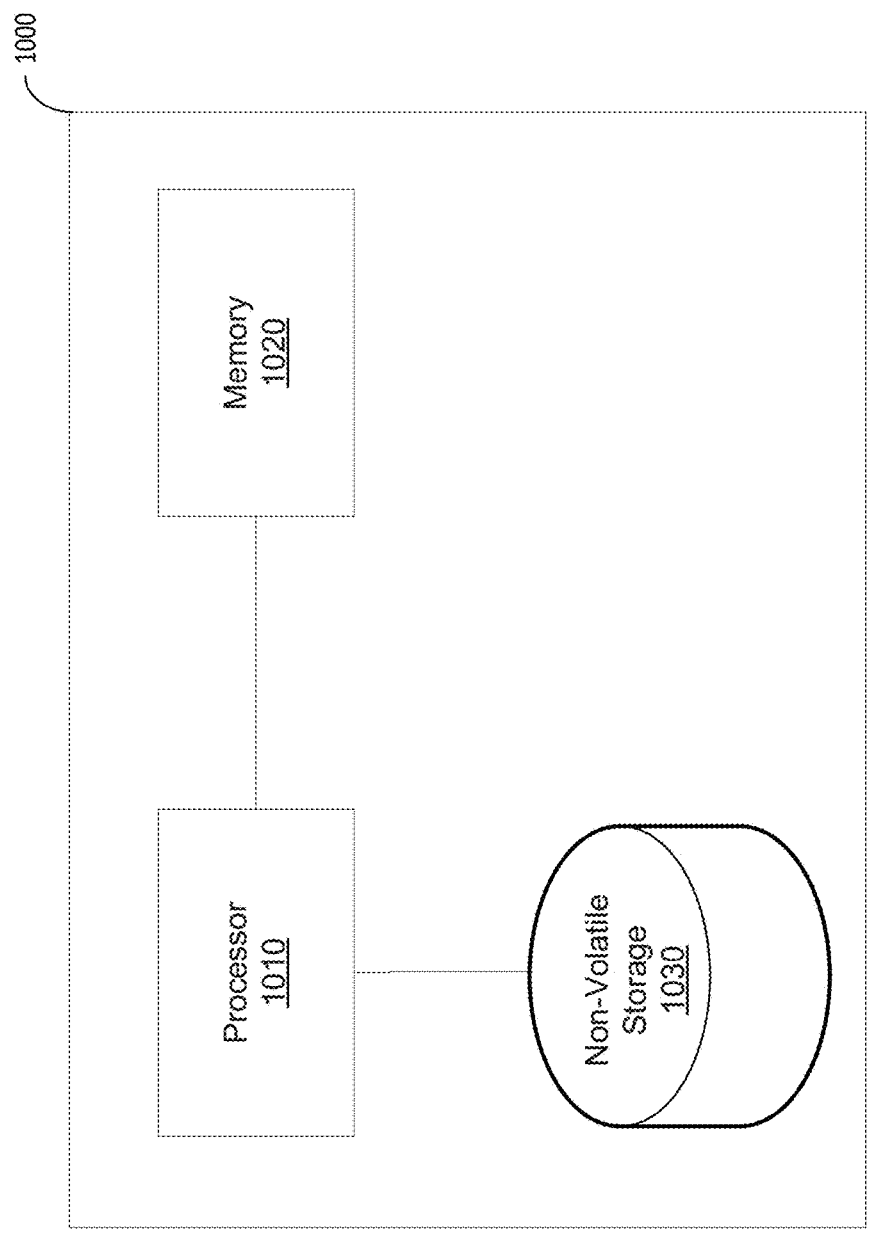
FIG. 10 is a diagram of an illustrative computer system that may be used in implementing some embodiments of the technology described herein.

An illustrative implementation of a computer system 1000 that may be used in connection with any of the embodiments of the disclosure provided herein is shown in FIG. 10. The computer system 1000 may include one or more processors

1010 and one or more articles of manufacture that comprise non-transitory computer-readable storage media (e.g., memory 1020 and one or more non-volatile storage media 1030). The processor 1010 may control writing data to and reading data from the memory 1020 and the non-volatile storage device 1030 in any suitable manner. To perform any of the functionality described herein, the processor 1010 may execute one or more processor-executable instructions stored in one or more non-transitory computer-readable storage media (e.g., the memory 1020), which may serve as non-transitory computer-readable storage media storing processor-executable instructions for execution by the processor 1010.

The terms "program" or "software" are used herein in a generic sense to refer to any type of computer code or set of processor-executable instructions that can be employed to program a computer or other processor to implement various aspects of embodiments as discussed above. Additionally, it should be appreciated that according to one aspect, one or more computer programs that when executed perform methods of the disclosure provided herein need not reside on a single computer or processor, but may be distributed in a modular fashion among different computers or processors to implement various aspects of the disclosure provided herein.

Processor-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in one or more non-transitory computer-readable storage media in any suitable form. For simplicity of illustration, data structures may be shown to have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Also, various inventive concepts may be embodied as one or more processes, of which examples (e.g., the processes described with reference to FIGS. 2, 9A, and 9B) have been provided. The acts performed as part of each process may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, and/or ordinary meanings of the defined terms.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the techniques described herein in detail, various modifications, and improvements will readily occur to those skilled in the art. Such modifications and improvements are intended to be within the spirit and scope of the disclosure. Accordingly, the foregoing description is by way of example only, and is not intended as limiting. The techniques are limited only as defined by the following claims and the equivalents thereto.

According to some aspects of the technology described herein a method of determining orientations and positions of segments of a multi-segment articulated rigid body system is provided, wherein one of the segments is anchored at an anchor point. In some embodiments, the method comprises: during a learning phase, receiving a first set of measurement data generated from movement sensors affixed to a non-anchored segment together with additional measurement data for determining an orientation and/or position of the non-anchored segment relative to the anchor point; processing, via a learning algorithm, the first set of measurement data and the additional measurement data to fit parameters of a statistical model from which estimates of the orientation and positioning of the non-anchored segment relative to the anchor point are derivable; during an analysis phase, receiving a second set of measurement data generated from the movement sensors affixed to the non-anchored segment of the articulated rigid body system; and applying the second set of measurement data against the statistical model to determine time-varying orientation and position of the non-anchored segment relative to the anchor point on the first segment.

In some embodiments, the movement sensors are one of: wearable electronic devices, and models (e.g. in the case of training with data from simulated sensors) of such wearable electronic devices.

In some embodiments, the statistical model is a neural network. In some embodiments, the neural network may be a recurrent neural network (e.g., a long short-term memory recurrent neural network). In some embodiments, the neural network may be a variational autoencoder.

In some embodiments, the non-anchored segment of the two-segment articulated rigid body system corresponds to a user's forearm, and the segment of the articulated rigid body system that is anchored at the anchor point corresponds to the user's upper arm.

In some embodiments, the first and second set of measurement data are associated with a same user. In some embodiments, the first set of measurement data is associated with a first user, and the second set of measurement data is associated with a second user that differs from the first user.

In some embodiments, the analysis phase occurs after the learning phase and in real-time.

In some embodiments, the method further includes providing to a host application, as an output, the position and orientation of the non-anchored segment of the multi-segment articulated rigid body system.

In some embodiments, the first set of measurement data is received from a first sensor affixed to a first segment of the articulated rigid body system, together with a second sensor affixed to a second segment of the articulated rigid body system.

Some embodiments provide for a method of determining the time-varying orientations and positions of segments of a two-segment articulated rigid body system, wherein a first segment is anchored at an anchor point to fix its position but not its orientation, and a second segment is connected for articulation relative to the first segment, the second segment being non-anchored, the method comprising: retrieving a statistical model, the statistical model having been generated during a training phase using a first set of measurement data generated from movement sensors affixed to at least the non-anchored segment, the statistical model having parameters that are fitted from the first set of measurement data and from which estimates of an orientation and position of the non-anchored segment relative to the anchor point are derivable; during an analysis phase, receiving a second set of measurement data generated from movement sensors affixed to the non-anchored segment of the two-segment articulated rigid body system; and applying the second set of measurement data against the statistical model to determine time-varying orientation and position of the non-anchored segment relative to the anchor point on the first segment.

In some embodiments, the parameters of the statistical model represent one or more constraints under which the articulated rigid body moves.

In some embodiments, the one or more constraints are biophysical constraints. In some embodiments, at least one constraint is imposed on the statistical model by anatomy. In some embodiments, at least one constraint is imposed on the statistical model by a statistical pattern of movement. In some embodiments, the statistical model is trained to determine a position of a movement sensor on the non-anchored segment, and wherein the method further includes using inverse kinematics to determine at least one aspect of an orientation of the first segment.

In some embodiments, the statistical model is trained to determine an orientation of the anchored segment, wherein the method further includes using forward kinematics to determine a position of the non-anchored segment.

Some embodiments provide for a multi-segment articulated rigid body system with up to n segments, a method to predict a position and orientation of at least one non-anchored rigid body segment, the method comprising: receiving measurement data generated from real or simulated sensors placed on only a subset of the segments; training a neural network based on the received measurement data; and using the neural network model, and in real-time, determining a time-varying orientation and position of the non-anchored rigid body segment relative to an anchor point.

What is claimed is as follows:

1. A computerized system for determining spatial information for a multi-segment articulated rigid body system having at least an anchored segment and a non-anchored segment connected to the anchored segment, the anchored segment anchored to an anchor point to fix a position of the anchored segment relative to a torso of a user, each segment in the multi-segment articulated rigid body system representing a respective body part of the user, the computerized system comprising:
   a first autonomous movement sensor;
   at least one computer hardware processor; and
   at least one non-transitory computer-readable storage medium storing processor-executable instructions that, when executed by the at least one computer hardware processor, cause the at least one computer hardware processor to perform:
      obtaining signals recorded by the first autonomous movement sensor when the first autonomous movement sensor is coupled to a body part of the user represented by the non-anchored segment, the obtained signals indicating a position and an orientation of the non-anchored segment and not indicating both a position and orientation of the anchored segment;
      providing the obtained signals as input to a trained statistical model and obtaining corresponding output of the trained statistical model; and
      determining, spatial information for the anchored segment based at least in part on the corresponding output of the trained statistical model, wherein the spatial information comprises position and orientation information of the anchored segment of the multi-segment articulated rigid body system.

2. The computerized system of claim 1, wherein determining the spatial information for the anchored segment and the non-anchored segment comprises:
   determining a spatial relationship between the anchored segment and the non-anchored segment.

3. The computerized system of claim 2, wherein determining the spatial relationship between the anchored segment and the non-anchored segment comprises:
   determining a set of one or more joint angles describing the spatial relationship between the anchored segment and the non-anchored segment.

4. The computerized system of claim 1, wherein the first autonomous movement sensor comprises an inertial measurement unit (IMU).

5. The computerized system of claim 1, wherein the first autonomous movement sensor comprises at least one sensor selected from the group consisting of a gyroscope, an accelerometer, and a magnetometer.

6. The computerized system of claim 1, wherein the trained statistical model comprises a trained non-linear regression model.

7. The computerized system of claim 1, wherein the trained statistical model comprises a trained recurrent neural network.

8. The computerized system of claim 1, wherein the trained statistical model comprises a trained variational autoencoder.

9. The computerized system of claim 1, wherein the first autonomous movement sensor is arranged on a single wearable device configured to be worn on or around a body part of the user.

10. The computerized system of claim 9, wherein the single wearable device comprises a flexible or elastic band configured to be worn around the body part of the user.

11. The computerized system of claim 1, wherein the processor-executable instructions, when executed by the at least one computer hardware processor, further cause the at least one computer hardware processor to perform:
sending one or more control signals to a controller configured to instruct a device to perform an action based on the one or more control signals.

12. The computerized system of claim 11, wherein the processor-executable instructions, when executed by the at least one computer hardware processor, further cause the at least one computer hardware processor to perform executing a computer application that provides a virtual reality environment,
wherein the controller comprises a display controller configured to instruct a display to display a visual representation of a character in the virtual reality environment, and
wherein the one or more control signals comprise signals to instruct the display controller to update in real time the visual representation of the character based, at least in part, on the determined spatial information.

13. The computerized system of claim 12, wherein the virtual reality environment comprises a virtual object and wherein updating the visual representation of the character based on the determined spatial information comprises updating the visual representation such that the character interacts with the virtual object.

14. The computerized system of claim 13, wherein interacting with the virtual object comprises an action selected from the group consisting of grasping the virtual object, dropping the virtual object, pushing the virtual object, throwing the virtual object, pulling the virtual object, opening the virtual object, and closing the virtual object.

15. The computerized system of claim 11, wherein the controller includes a control interface for a physical device, and wherein the one or more control signals comprise signals to instruct at least one component of the physical device to move based on the determined spatial information.

16. The computerized system of claim 1, wherein the processor-executable instructions, when executed by the at least one computer hardware processor, further cause the at least one computer hardware processor to perform:
updating a computer-generated skeletal representation of the multi-segment articulated rigid body system based, at least in part, on the determined spatial information; and
storing, on the at least one non-transitory computer-readable storage medium, the updated computer-generated representation of the multi-segment articulated rigid body system.

17. A method for determining spatial information for determining spatial information for a multi-segment articulated rigid body system having at least an anchored segment and a non-anchored segment connected to the anchored segment, the anchored segment anchored to an anchor point to fix a position of the anchored segment relative to a torso of a user, each segment in the multi-segment articulated rigid body system representing a respective body part of the user, the method comprising:
obtaining signals recorded by a first autonomous movement sensor when the first autonomous movement sensor is coupled to a body part of the user represented by the non-anchored segment, the obtained signals indicating a position and an orientation of the non-anchored segment and not indicating both a position and orientation of the anchored segment;
providing the obtained signals as input to a trained statistical model and obtaining corresponding output of the trained statistical model; and
determining spatial information for the anchored segment based at least in part on the corresponding output of the trained statistical model, wherein the spatial information comprises position and orientation information of the anchored segment of the multi-segment articulated rigid body system.

18. A computerized system for training a statistical model for generating spatial information for a multi-segment articulated rigid body system having at least an anchored segment and a non-anchored segment connected to the anchored segment, the anchored segment anchored to an anchor point to fix a position of the anchored segment relative to a torso of a user, each segment in the multi-segment articulated rigid body system representing a respective body part of the user, the computerized system comprising:
a plurality of autonomous movement sensors;
at least one computer hardware processor; and
at least one non-transitory computer-readable storage medium storing processor-executable instructions that, when executed by the at least one computer hardware processor, causes the at least one computer hardware processor to perform:
obtaining movement signals recorded by the plurality of autonomous movement sensors when each of the plurality of autonomous movement sensors is coupled to a body part of a first user represented by a respective segment in the multi-segment articulated rigid body system, the movement signals indicating a position of an orientation of the non-anchored segment and not indicating both a position and orientation of the anchored segment;
generating training data using the obtained movement signals;
training the statistical model using at least some of the generated training data to output a trained statistical model, wherein the trained statistical model is configured to:
generate spatial information for a multi-segment articulated rigid body system using movement signals obtained by a single movement sensor coupled to a non-anchored segment of a body part of a second user, and generate the spatial information for the anchored segment wherein the spatial information comprises position and orientation information of the anchored segment of the multi-segment articulated rigid body system; and storing the trained statistical model.

19. The computerized system of claim 18, wherein the first user and the second user are a same user.

* * * * *